(12) United States Patent
Tang et al.

(10) Patent No.: US 11,006,998 B2
(45) Date of Patent: May 18, 2021

(54) SYSTEMS, METHODS, AND MEDIA FOR WIRELESS RADIO FREQUENCY LESIONING

(71) Applicant: The Brigham and Women's Hospital, Inc., Boston, MA (US)

(72) Inventors: Sai Chun Tang, Auburndale, MA (US); Michael Vaninetti, La Jolla, CA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 435 days.

(21) Appl. No.: 15/885,739

(22) Filed: Jan. 31, 2018

(65) Prior Publication Data

US 2018/0214194 A1    Aug. 2, 2018

Related U.S. Application Data

(60) Provisional application No. 62/453,134, filed on Feb. 1, 2017.

(51) Int. Cl.
*A61B 18/12* (2006.01)
*A61B 18/14* (2006.01)
(Continued)

(52) U.S. Cl.
CPC .......... *A61B 18/1206* (2013.01); *A61B 18/14* (2013.01); *A61B 2018/0044* (2013.01);
(Continued)

(58) Field of Classification Search
CPC ............ A61B 2018/1286; A61B 18/14; A61B 2090/0815; A61B 2560/0219;
(Continued)

(56) References Cited

U.S. PATENT DOCUMENTS 5,585,723 A * 12/1996 Withers ................. G01R 33/34
324/318
5,697,909 A * 12/1997 Eggers ................... A61B 18/12
604/114

(Continued)

OTHER PUBLICATIONS

Allen, T.H., et al, "Density, fat, water and solids in freshly isolated tissues," Journal of Applied Physiology, vol. 14, No. 6, Nov. 1959, pp. 1005-1008.

(Continued)

*Primary Examiner* — Ronald Hupczey, Jr.
(74) *Attorney, Agent, or Firm* — Quarles & Brady LLP

(57) ABSTRACT

Systems, methods, and media for wireless radio frequency lesioning are provided. In some embodiments, a system for wireless radio frequency comprises: a wireless radiofrequency device, comprising: a receiving coil, a plurality of capacitors coupled in parallel to the receiving coil, a first electrode, and a second electrode, wherein a capacitor of the plurality of capacitors is connected between the first electrode and the second electrode, and wherein capacitances of the plurality of capacitors cause the receiving coil to pair with a transmitter at an operating frequency; a transmitter comprising at least one transmitting coil; and a radiofrequency generator configured to apply a radiofrequency signal at the operating signal to the transmitter.

25 Claims, 18 Drawing Sheets

(51) Int. Cl.
A61B 18/00 (2006.01)
H04B 1/40 (2015.01)
A61B 90/00 (2016.01)

(52) U.S. Cl.
CPC ............... *A61B 2018/00577* (2013.01); *A61B 2018/00791* (2013.01); *A61B 2018/00875* (2013.01); *A61B 2018/126* (2013.01); *A61B 2018/1286* (2013.01); *A61B 2090/0815* (2016.02); *A61B 2560/0219* (2013.01); *H04B 1/40* (2013.01)

(58) Field of Classification Search
CPC ........... A61B 2018/00892; A61B 2018/00845; A61B 2018/00875; H04B 1/40; H04B 1/568; H04B 1/561
See application file for complete search history.

(56) References Cited

U.S. PATENT DOCUMENTS

| | | | | |
|---|---|---|---|---|
| 6,802,857 | B1* | 10/2004 | Walsh | A61F 2/86 623/1.15 |
| 8,669,770 | B2* | 3/2014 | Cros | A61B 5/0031 324/601 |
| 9,717,552 | B2* | 8/2017 | Cosman | A61B 18/1482 |
| 2005/0027192 | A1* | 2/2005 | Govari | A61B 5/06 600/424 |
| 2006/0009815 | A1* | 1/2006 | Boveja | A61N 1/08 607/45 |
| 2008/0027505 | A1 | 1/2008 | Levin | |
| 2010/0264748 | A1 | 10/2010 | Tucker | |
| 2012/0158078 | A1* | 6/2012 | Moulder | A61N 1/3718 607/9 |
| 2012/0262108 | A1* | 10/2012 | Olson | H02J 7/025 320/108 |
| 2015/0244178 | A1 | 8/2015 | Tang | |
| 2015/0265342 | A1* | 9/2015 | Long | A61B 18/1206 606/41 |
| 2016/0204645 | A1 | 7/2016 | Mitcheson | |

OTHER PUBLICATIONS

Bartlett, R., et al, Encyclopedia of International Sports Studies, Routledge, p. 164, 2009.
Cosman, E.R. et al, "Bipolar radiofrequency lesion geometry: implications for palisade treatment of sacroiliac joint pain," Pain Practice, vol. 11, No. 1, Jan. 2011, pp. 3-22.
Gabriel C., "Compilation of the dielectric properties of body tissues at RF and microwave frequencies," Air Force Material Command, Brooks Air Force Base, Texas, AL/OE-TR-1996- 0037, 1996.
Head, HW, et al, "Thermal ablation for hepatocellular carcinoma," Gastroenterology, vol. 127, No. 5, Nov. 2004, pp. S167-S178.
Hillen, T. J., et al, "Treatment of metastatic posterior vertebral body osseous tumors by using a targeted bipolar radiofrequency ablation device: technical note," Radiology, vol. 273, No. 1, Oct. 2014, pp. 261-267.
Hubbell, J.H, et al, X-Ray Mass Attenuation Coefficients, NIST Standard Reference Database 126, last updated Jul. 2004, accessed online on Apr. 30, 2019 at http://physics.nist.gov/PhysRefData/XrayMassCoef/tab2.html.
Center for NMR Research Software, RF_Tools, accessed online Apr. 30, 2019 at http://www.pennstatehershey.org/web/nmrlab/resources/software/rftools.
Medtronic, Implant Manual: RestoreSensor® SureScan® MRI 97714 Rechargeable neurostimulator, Medtronic, 2013.
International Search Report and Written Opinion for PCT/US2018/016487, dated May 8, 2018, 20 pages.
Kim, L., Tang, S. C., Yoo S. S., "Prototype modular capsule robots for capsule endoscopies," IEEE ICCAS 2013.

Kramer, R., et al, "All about FAX a Female Adult voXel phantom for Monte Carlo calculation in radiation protection dosimetry", Physics in Medicine and Biology, vol. 49, No. 23, Dec. 2004, pp. 5203-5216.
Lencioni R., et al., "Earlystage hepatocellular carcinoma in patients with cirrhosis: Long-term results of percutaneous image-guided radiofrequency ablation," Radiology, vol. 234, No. 3, Mar. 2005, pp. 961-967.
Liliang, P. C. et al, "Pulsed radiofrequency lesioning of the suprascapular nerve for chronic shoulder pain: a preliminary report," Pain Medicine, vol. 10, No. 1, Jan.-Feb. 2009, pp. 70-75.
Livraghi, T. et al, "Small hepatocellular carcinoma: Treatment with radio-frequency ablation versus ethanol injection," Radiology, vol. 210, No. 3, Mar. 1999, pp. 655-661.
McDannold, N. et al, "MRI investigation of the threshold for thermally induced blood-brain barrier disruption and brain tissue damage in the rabbit brain," Magnetic Resonance in Medicine, vol. 51, No. 5, May 2004, pp. 913-923.
Moroz, P. et al, "Magnetically mediated hyperthermia: current status and future directions," International Journal of Hyperthermia, vol. 18, No. 4, Jul. 2002, pp. 267-284.
Nash T. P., "Percutaneous Radiofrequency Lesioning of Dorsal-Root Ganglia for Intractable Pain," Pain, vol. 24, No. 1, Jan. 1986, pp. 67-73.
Nath, S. et al, "Percutaneous lumbar zygapophysial (Facet) joint neurotomy using radiofrequency current, in the management of chronic low back pain—A randomized double-blind trial," Spine, vol. 33, No. 12, May 2008, pp. 1291-1297.
Navani, A., et al, "A case of pulsed radiofrequency lesioning for occipital neuralgia," Pain Medicine, vol. 7, No. 5, Oct. 2006, pp. 453-456.
Nebuya, S., et al, "Indirect measurement of lung density and air volume from electrical impedance tomography (EIT) data," Physiological Measurement, vol. 32, No. 12, Dec. 2011, pp. 1953-1967.
Niwa, T. et al, "Implant hyperthermia resonant circuit produces heat in response to MRI unit radiofrequency pulses," British Journal of Radiology, vol. 81, No. 961, Jan. 2008, pp. 69-72.
Omata, M., et al, "Treatment of hepatocellular carcinoma by percutaneous tumor ablation methods: Ethanol injection therapy and radiofrequency ablation," Gastroenterology, vol. 127, No. 5, Nov. 2004, pp. S159-S166.
Psathas, K.A., et al, "Operation of ingestible antennas along the gastrointestinal tract: Detuning and performance," 13th IEEE International Conference on Bioinformatics and BioEngineering (BIBE), Nov. 2013.
Puers, et al, "Wireless power and data transmission strategies for next-generation capsule endoscopes," J. Micromech Microeng., 2011.
Shanthanna, H., et al, "Assessing the effectiveness of 'pulse radiofrequency treatment of dorsal root ganglion' in patients with chronic lumbar radicular pain: study protocol for a randomized control trial," Trials, vol. 13, No. 52, Apr. 2012.
Shiozawa, K, et al, "Comparison of percutaneous radiofrequency ablation and CyberKnife (R) for initial solitary hepatocellular carcinoma: A pilot study," World Journal of Gastroenterology, vol. 21, No. 48, Dec. 2015, pp. 13490-13499.
Simopoulos, T. T., et al, "Response to Pulsed and Continuous Radio frequency Lesioning of the Dorsal Root Ganglion and Segmental Nerves in Patients with Chronic Lumbar Radicular Pain," Pain Physician, vol. 11, No. 2, Mar.-Apr. 2008, pp. 137-144.
Stauffer, P.R., et al, "Magnetic induction heating of ferromagnetic implants for inducing localized hyperthermia in deep-seated tumors," IEEE Transactions on Biomedical Engineering, vol. BME-31, No. 2, Feb. 1984, pp. 235-251.
Stauffer, P.R., et al, "Observations on the use of ferromagnetic implants for inducing hyperthermia," IEEE Transactions on Biomedical Engineering, vol. 31, No. 1, Jan. 1984, pp. 76-90.
Stauffer, P.R., et al, "Practical induction heating coil designs for clinical hyperthennia with ferromagnetic implants," IEEE Transactions on Biomedical Engineering, vol. 41, No. 1, Jan. 1994, pp. 17-28.

(56) References Cited

OTHER PUBLICATIONS

Takura, T. et al, "Miniaturization of Micro Implantable Devices With Thermosensitive Ferrite for Soft-Heating Hyperthermia," IEEE Transactions on Magnetics, vol. 43, No. 6, Jun. 2007, pp. 2454-2456.

Tang, Sai Chun, et al. "Intermediate range wireless power transfer with segmented coil transmitters for implantable heart pumps." IEEE Transactions on Power Electronics 32.5 (2017): 3844-3857.

Tang S. C. et al, "Power loss analysis and comparison of segmented and unsegmented energy coupling coils for wireless energy transfer," IEEE Journal of Emerging and Selected Topics in Power Electronics. vol. 3, No. 1, Mar. 2015, pp. 215-225.

Tang SC, "A low-operating-voltage wireless intermediate-range scheme for energy and signal transmission by magnetic coupling for implantable devices," IEEE Journal of Emerging and Selected Topics in Power Electronics. vol. 3, No. 1, Mar. 2015, pp. 242-251.

Xin, W. et al, "Study of a wireless power transmission system for an active capsule endoscope," Int. J. Med. Robot. Comput. Assist. Surgery, 2010.

Yan, S, et al, "A simulation study to compare the phase-shift angle radiofrequency ablation mode with bipolar and unipolar modes in creating linear lesions for atrial fibrillation ablation," International Journal of Hyperthermia, vol. 32, No. 3, Feb. 2016, pp. 231-238.

\* cited by examiner

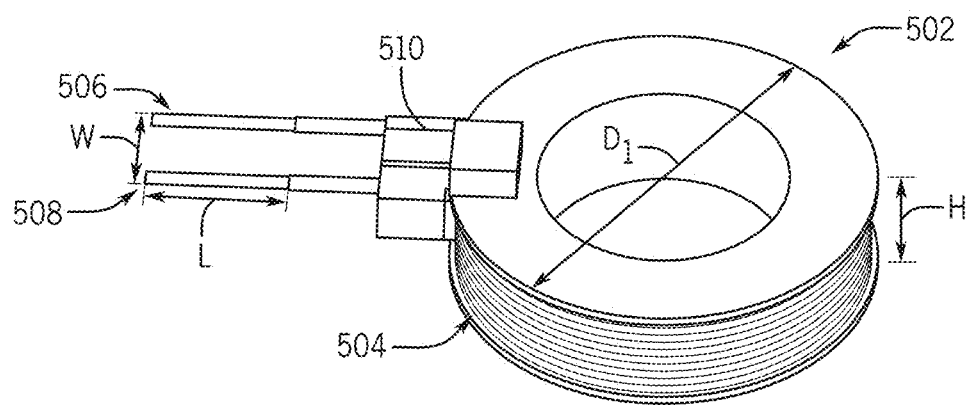
FIG. 5A
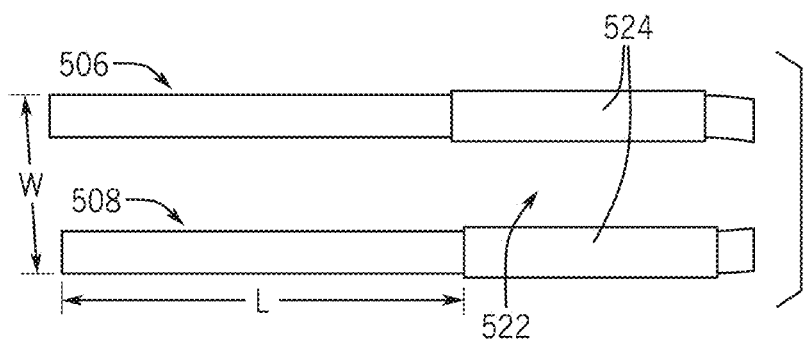
FIG. 5B
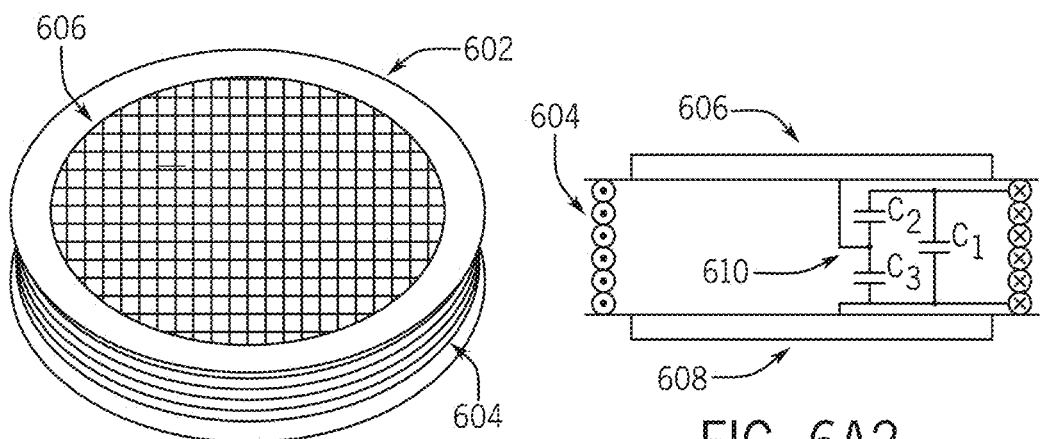
FIG. 6A1
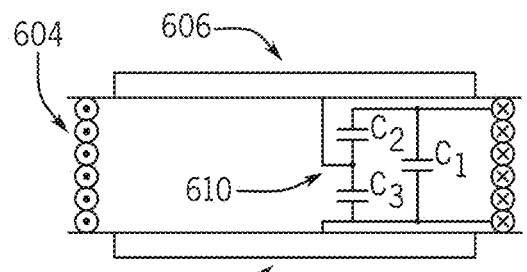
FIG. 6A2

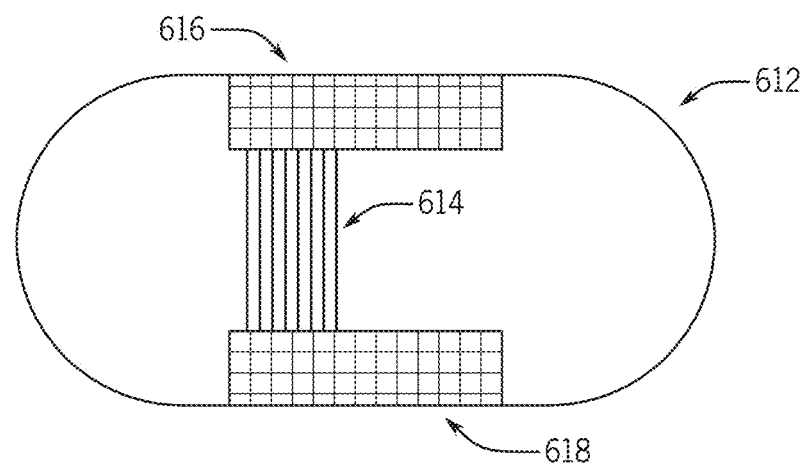
FIG. 6B1
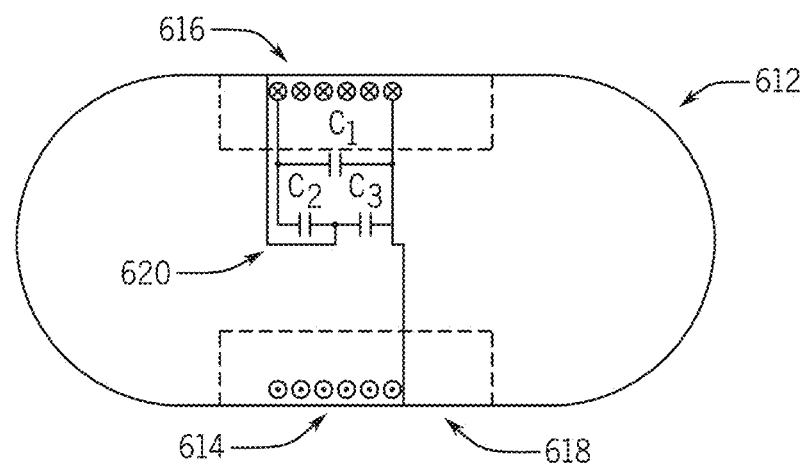
FIG. 6B2

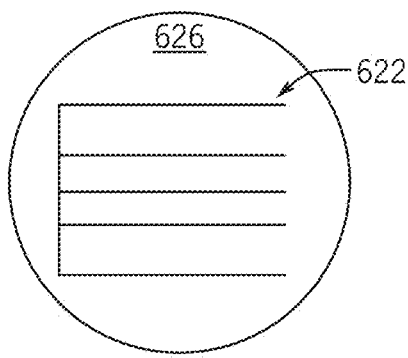
FIG. 6C1
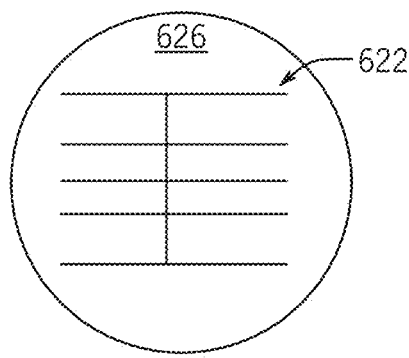
FIG. 6C2
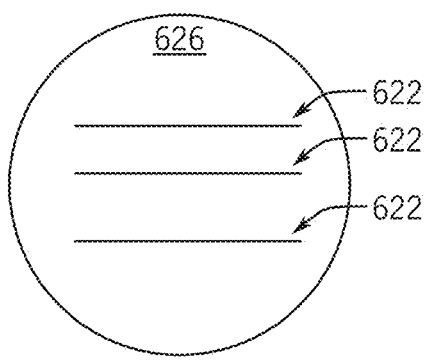
FIG. 6C3
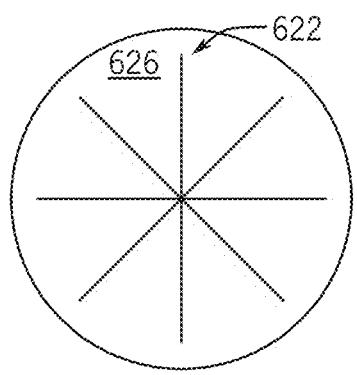
FIG. 6C4
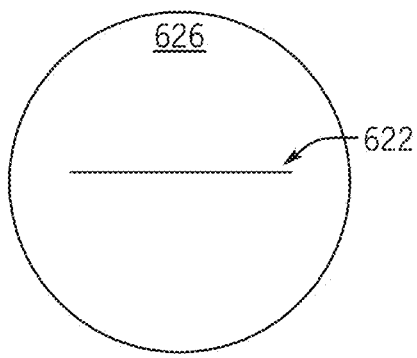
FIG. 6C5
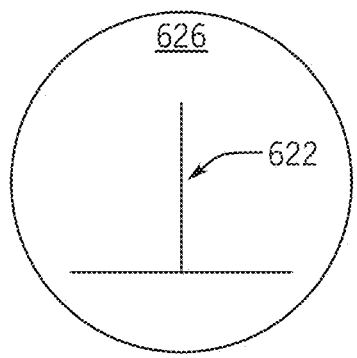
FIG. 6C6

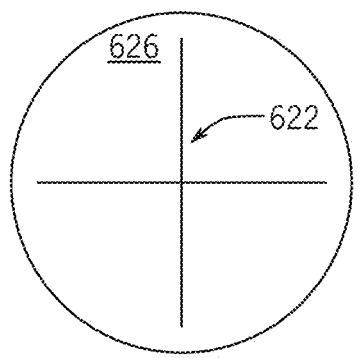
FIG. 6C7
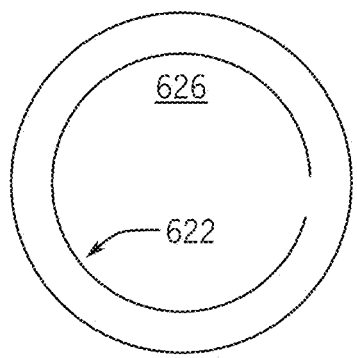
FIG. 6C8
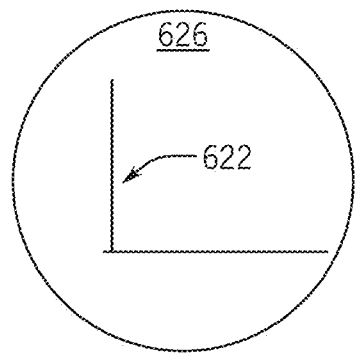
FIG. 6C9
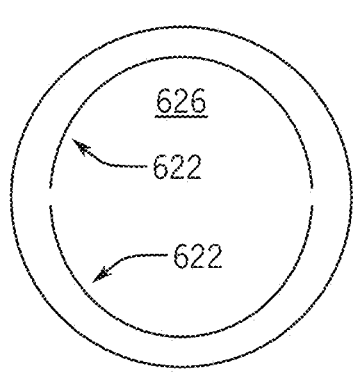
FIG. 6C10
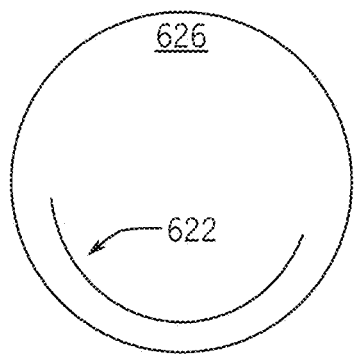
FIG. 6C11
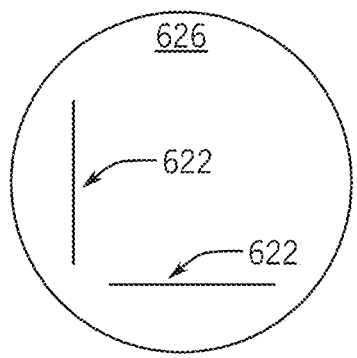
FIG. 6C12

SYSTEMS, METHODS, AND MEDIA FOR WIRELESS RADIO FREQUENCY LESIONING

CROSS-REFERENCE TO RELATED APPLICATIONS

This application is based on, claims the benefit of, and claims priority to U.S. Provisional Application No. 62/453,134, filed Feb. 1, 2017, which is hereby incorporated herein by reference in its entirety for all purposes.

STATEMENT REGARDING FEDERALLY SPONSORED RESEARCH

N/A

BACKGROUND

Radio frequency lesioning (RFL) has been used to treat a variety of diseases by ablating tissue, such as cancer or pain-signaling nerve tissue. RFL of nerve tissue, for example, is a common procedure used to treat several different pain syndromes afflicting millions of patients per year.

FIG. 1 shows an example of a RFL system that can be used for ablating nerve tissue. A conventional RF nerve lesioning treatment can include inserting a percutaneous electrode 102 to the target nerve tissue in a subject 104, and a placing a grounding pad 108 on the arm or leg of subject 104. A radio frequency generator 106 can be used to apply an RF signal to electrode 102, and an RF current 110 flows between electrode 102 and grounding pad 108.

FIG. 2 shows an example of a portion of the conventional radio frequency lesioning system of FIG. 1. As shown in FIG. 2, a tip of electrode 102 is inserted near a nerve 202. RF current 110 is strongest around the tip of electrode 102 and generates heat 204, which causes protein denaturation and cell death, blocking nerve 202 from sending pain signals to the brain. However, nerve 202 often regenerates from the lesioning and the pain returns, necessitating repeated procedures (e.g., two to six times per year) to maintain pain relief. Due to the necessity of inserting a wired electrode (e.g., electrode 102) each RF nerve ablation treatment using conventional RFL must be performed in a clinical setting by a skilled professional (e.g., an anesthesiologist). Accordingly, repeated procedures are costly to perform, increase the risk of the subject experiencing complications, and often leads to the subject experiencing significant pain at some point between treatments when pain starts to return but a procedure cannot be immediately scheduled.

An implantable tissue-lesioning device that is powered wirelessly or with an implantable battery would provide an alternative approach that would avoid repeated percutaneous procedures. Using such a device, a patient could undergo one initial procedure to implant the device in or near the target tissue, then wirelessly receive lesioning treatments as needed. However, while wirelessly powered implantable devices have been proposed in the past, each has drawbacks that would limit its effectiveness for use in tissue-lesioning. For example, one proposed device is made of stainless steel or ferrite rods, and an external energy transmitting coil is used to apply an alternating magnetic field to induce eddy currents in the ferromagnetic rods, which heats the implant and adjacent tissue. An alternative proposal was implant a thermosensitive ferrite rod with a metallic ring coating, where the ferrite material was used to concentrate the magnetic field, which then induced current in the metallic rings heating the implant and the adjacent tissue. In such a device, when the implant temperature reached the Curie-point of the material, the magnetic flux density in the ferrite rod and the ring current decreased, allowing the implant to self-regulate temperature near the Curie-point. In both of these devices, however, the magnetic field was generated by an energy-transmitting coil wrapped around the patient's body, and the necessary excitation voltage to perform radio frequency lesioning would be excessively high. For example, coil voltages up to 30 kilovolts (kV) would be required to produce sufficient magnetic field strength for heating up such implants to perform wireless radio frequency lesioning, which may cause damage to tissue that is not being targeted, and may create significant amounts of waste heat from the high coil voltage. While one system used a transmitting coil made of copper tubing to allow circulating water coolant to carry away heat generated by the high-voltage coil, this system would not address the potential damage caused by the high coil voltage. Instead, use of such systems would require protective equipment, such as a bulky Faraday shield to avoid undesired temperature rise in superficial tissue caused by the strong electric field (e.g., on the order of 2 kV/centimeter (cm)). The high coil voltage would also pose other serious safety issues (e.g., risk of electrocution), and increases the manufacturing cost of any such system due to the expense associated with high-voltage RF drivers, isolation systems, and circulating water coolant systems.

An alternative implantable heater powered by the magnetic field generated by the RF coil in a magnetic resonance imaging (MRI) system has also proposed. However, the receiver temperature rise was less than 13 degrees Celsius (° C.), which would not be sufficient to lesion target tissue, and using an MRI machine for lesioning tissue would be a very costly, as MRI machines are expensive to maintain, and any other uses would have to compete for time with in high value imaging procedures. None of these systems offers a promising solution to provide wireless radio frequency lesioning.

Accordingly, systems, methods, and media for wireless radio frequency lesioning are desirable.

SUMMARY

In accordance with some embodiments of the disclosed subject matter, systems, methods, and media for wireless radio frequency lesioning are provided.

In accordance with some embodiments of the disclosed subject matter, a wireless radiofrequency device is provided, the wireless radiofrequency device comprising: a receiving coil; a plurality of capacitors coupled in parallel to the receiving coil; a first electrode; and a second electrode, wherein a capacitor of the plurality of capacitors is connected between the first electrode and the second electrode, and wherein capacitances of the plurality of capacitors cause the receiving coil to pair with a transmitter at an operating frequency.

In some embodiments, the plurality of capacitors comprises: a first capacitor connected in parallel with the receiving coil; a second capacitor and the capacitor connected in series with one another, the second capacitor and the capacitor connected in parallel with the first capacitor and with the receiving coil.

In some embodiments, the second capacitor and the capacitor form a potential divider to provide a first portion of an input potential to the first electrode and a second portion of the input potential to the second electrode.

In some embodiments, the receiving coil comprises a plurality of turns.

In some embodiments, each turn comprises a plurality of enameled wires connected in parallel.

In some embodiments, the operating frequency is about 6.78 megahertz (MHz).

In some embodiments, the plurality of capacitors comprise capacitors with capacitances of 6 nanofarads, 470 picofarads, and 638 picofarads.

In some embodiments, the first electrode comprises a wire connected to between two of the plurality of capacitors at a first end, and terminating at a second end without connecting to another component.

In some embodiments, the first electrode comprises a wire having a diameter of between about 30 American wire gauge (AWG) and about 10 AWG.

In some embodiments, a first portion of the first electrode extending from the first end is insulated, and a second portion extending from the second end toward the first portion is not insulated.

In some embodiments, the receiving coil has an exterior diameter of less than about 2.5 centimeters.

In some embodiments, the first electrode and the second electrode a separated by a gap.

In some embodiments, the gap is about 5 millimeters.

In some embodiments, the wireless radiofrequency device is configured to be implanted in a subject adjacent to tissue to be lesioned, and to wirelessly receive power from a radio transmitter which causes tissue between and around the electrodes to be heated to at least 55 degrees Celsius.

In some embodiments, the wireless radiofrequency device further comprises: a temperature sensor that outputs a temperature signal; and a switch that, when closed, causes an electrical component to be connected in parallel with the receiving coil, wherein a state of the switch is controlled based on the temperature signal.

In some embodiments, the electrical component has an impedance that, when connected in parallel with the receiving coil, causes the receiving coil to be detuned from the operating frequency.

In some embodiments, the first electrode is disposed at a first end of the receiving coil.

In accordance with some embodiments of the disclosed subject matter, a wireless radiofrequency device is provided, the wireless radiofrequency device comprising: a receiving coil having a first end and a second end; a first capacitor connected between the first end of the receiving coil and the second end of the receiving coil; a second capacitor connected between the first end of the receiving coil and a first end of a first electrode; a third capacitor connected between the first electrode and the second end of the receiving coil; and a second electrode having a first end connected to the second end of the receiving coil and the third capacitor, wherein a connection forms between the first electrode and the second electrode through tissue of a subject in which the wireless radiofrequency device is implanted.

In accordance with some embodiments of the disclosed subject matter, a wireless radiofrequency system is provided, the wireless radiofrequency system comprising: a wireless radiofrequency device, comprising: a receiving coil; a plurality of capacitors coupled in parallel to the receiving coil; a first electrode; and a second electrode, wherein a capacitor of the plurality of capacitors is connected between the first electrode and the second electrode, and wherein capacitances of the plurality of capacitors cause the receiving coil to pair with a transmitter at an operating frequency; a transmitter comprising at least one transmitting coil; and a radiofrequency generator configured to apply a radiofrequency signal at the operating signal to the transmitter.

In some embodiments, the at least one transmitting coil comprises at least one turn that is segmented by at least one capacitor connected between adjacent segments.

In some embodiments, the at least one turn is segmented into four segments, and comprises four 765 picofarad resonant capacitors each connecting two adjacent segments.

In some embodiments, the at least one transmitting coil comprises a first transmitting coil and a second transmitting coil arranged to form a Helmholtz coil.

In some embodiments, the radiofrequency signal has a root mean square current of less than about 1.7 amperes (Arms).

In accordance with some embodiments of the disclosed subject matter, a method for wireless radiofrequency lesioning is provided, the method comprising: implanting a wireless radiofrequency lesioning device within a subject, wherein the wireless radiofrequency lesioning device comprises: a receiving coil; a plurality of capacitors coupled in parallel to the receiving coil; a first electrode; and a second electrode, wherein a capacitor of the plurality of capacitors is connected between the first electrode and the second electrode, and wherein capacitances of the plurality of capacitors cause the receiving coil to pair with a transmitter at an operating frequency; positioning, subsequent to implanting the wireless radiofrequency lesioning device within the subject, the subject near a transmitting coil; causing a radiofrequency signal to be applied to the transmitting coil at the operating frequency; and lesioning a portion of tissue near the wireless radiofrequency device by applying the radiofrequency signal to the transmitting coil until the portion of tissue near the wireless radiofrequency device reaches a temperature of at least 55 degrees Celsius.

In some embodiments, the method further comprises: measuring a coil impedance of the transmitter; determining, based on the measured coil impedance, that the portion of tissue has reached a temperature of at least 55 degrees Celsius; and in response to determining that the portion of tissue has reached the temperature of at least 55 degrees Celsius, inhibiting the radiofrequency signal from being applied to the transmitting coil.

In some embodiments, a method for wireless pulsed radiofrequency lesioning is provided, the method comprising: implanting a wireless radiofrequency lesioning device within a subject, wherein the wireless radiofrequency lesioning device comprises: a receiving coil; a plurality of capacitors coupled in parallel to the receiving coil; a first electrode; and a second electrode, wherein a capacitor of the plurality of capacitors is connected between the first electrode and the second electrode, and wherein capacitances of the plurality of capacitors cause the receiving coil to pair with a transmitter at an operating frequency; positioning, subsequent to implanting the wireless radiofrequency lesioning device within the subject, the subject near a transmitting coil; causing a pulsed radiofrequency signal to be applied to the transmitting coil at the operating frequency; and inhibiting the pulsed radiofrequency signal from being applied to the transmitting coil.

In accordance with some embodiments of the disclosed subject matter, a non-transitory computer-readable medium containing computer executable instructions that, when executed by a processor, cause the processor to perform a method for wireless pulsed radiofrequency lesioning is provided, the method comprising: causing a radiofrequency signal to be applied to a transmitting coil at an operating frequency of an implanted wireless radiofrequency lesioning device within a subject, wherein the wireless radiofrequency lesioning device comprises: a receiving coil; a plurality of capacitors coupled in parallel to the receiving coil; a first electrode; and a second electrode, wherein a capacitor of the plurality of capacitors is connected between the first electrode and the second electrode, and wherein capacitances of the plurality of capacitors cause the receiving coil to pair with a transmitter at an operating frequency; measuring a coil impedance of the transmitter; determining, based on the measured coil impedance, that a portion of tissue near the wireless radiofrequency lesioning device has reached a predetermined temperature; and in response to determining that the portion of tissue has reached the predetermined temperature, inhibiting the radiofrequency signal from being applied to the transmitting coil.

In some embodiments, the predetermined temperature is a temperature between about 55 degrees Celsius and about 80 degrees Celsius.

In accordance with some embodiments of the disclosed subject matter, a wireless radiofrequency lesioning device is provided, the wireless radiofrequency lesioning device comprising: means for forming a receiving coil; a plurality of means for providing a capacitance, wherein the plurality of means for coupled in parallel to the means for forming a receiving coil; a first means for forming an electrode; and a second means for forming an electrode, wherein one of the plurality of means for providing a capacitance of the plurality of means is connected between the first electrode and the second electrode, and wherein capacitances of the plurality of means cause the receiving coil to pair with a transmitter at an operating frequency.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 5A shows an example of a wireless radio frequency lesioning device in accordance with some embodiments of the disclosed subject matter.

FIG. 5B shows an example of electrodes of a wireless radio frequency lesioning device in accordance with some embodiments of the disclosed subject matter.

FIG. 6A1 shows an example of another wireless radio frequency lesioning device in accordance with some embodiments of the disclosed subject matter.

FIG. 6A2 shows an example cross-sectional schematic diagram of the wireless radio frequency lesioning device of FIG. 6A1 in accordance with some embodiments of the disclosed subject matter.

FIG. 6B1 shows an example of another wireless radio frequency lesioning device in accordance with some embodiments of the disclosed subject matter.

FIG. 6B2 shows an example cross-sectional schematic diagram of the wireless radio frequency lesioning device of FIG. 6B1 in accordance with some embodiments of the disclosed subject matter.

FIGS. 6C1 to 6C12 show various example electrode shapes that can be used in connection with device wireless radiofrequency lesioning devices in accordance with some embodiments of the disclosed subject matter.

FIG. 12 shows an example of an implanted wireless radio frequency lesioning device in accordance with some embodiments of the disclosed subject matter.

DETAILED DESCRIPTION

Figure 1:
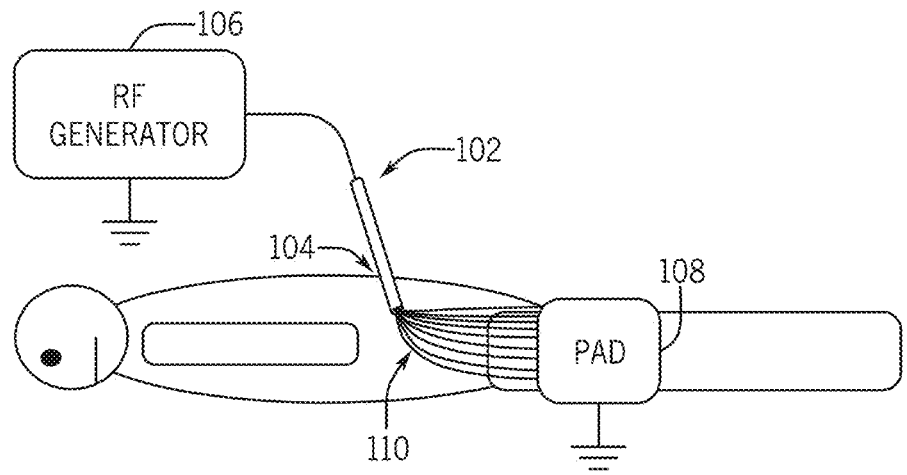
FIG. 1 shows an example of a conventional radio frequency lesioning system.

In accordance with some embodiments of the disclosed subject matter, mechanisms (which can include systems, methods and/or media) for wireless radio frequency lesioning are provided.

In some embodiments, the mechanisms described herein can be used to implement a relatively low-cost, implantable radio frequency lesioning device. In some embodiments, this can eliminate the need for repeated conventional RFL procedures. In some embodiments, a subject can undergo one initial procedure to implant a device implemented using the mechanisms described herein in the vicinity of the target tissue, and subsequent treatments can be performed by placing the subject in proximity of a portable transmitter for a relatively short period of time (e.g., a few minutes).

As subsequent treatments do not involve electrode insertion through the skin, performing wireless RFL procedures using the mechanisms described herein can eliminate the risk of bleeding or infection that would typically be present when performing additional wired RFL procedures. In some embodiments, the mechanisms described herein can use a transmitter that, unlike a conventional energy transmitting coil that required tens of kV, uses a significantly reduced voltage over the coil (e.g., less than 10 $V_{rms}$). In some such embodiments, the transmitter can be portable, as it can be powered by a wall outlet, and does not require bulky equipment for forced cooling, such as a circulating water coolant system. In some embodiments, an energy receiver implemented using the mechanisms described herein can be a 2.4-cm diameter coil tuned to the operating frequency of a transmitting coil to facilitate high power transfer while using a small implant, and a relatively low magnetic field strength.

In some embodiments, an implanted device implemented using the mechanisms described herein can automatically receive the energy wirelessly, and lesion the target tissue in the proximity of the implanted device. In some embodiments, an implanted device implemented using the mechanisms described herein can use bipolar RFL electrodes, rather than a monopolar electrode and a distant ground pad used in conventional RFL systems, which can reduce the size of the implanted device. In some embodiments, the mechanisms described herein can use bipolar electrodes implemented using two metal wires, which are electrically connected to an energy receiving coil. As the voltage received by the receiving coil is already at radio frequency, the implanted device can lesion adjacent tissue without a rectifier or an RF generator. Additionally, since an implantable device implemented using the mechanisms described herein can be powered wirelessly by a small receiving coil (i.e., it does not require an embedded battery), manufacturing costs can be reduced, and surgeries to replace such a battery can be avoided. This can result in an implantable wireless RFL device that uses relatively little power (e.g., compared to previously proposed wireless RFL systems), that is relatively small, and that is relatively easy to manufacture.

Figure 3:
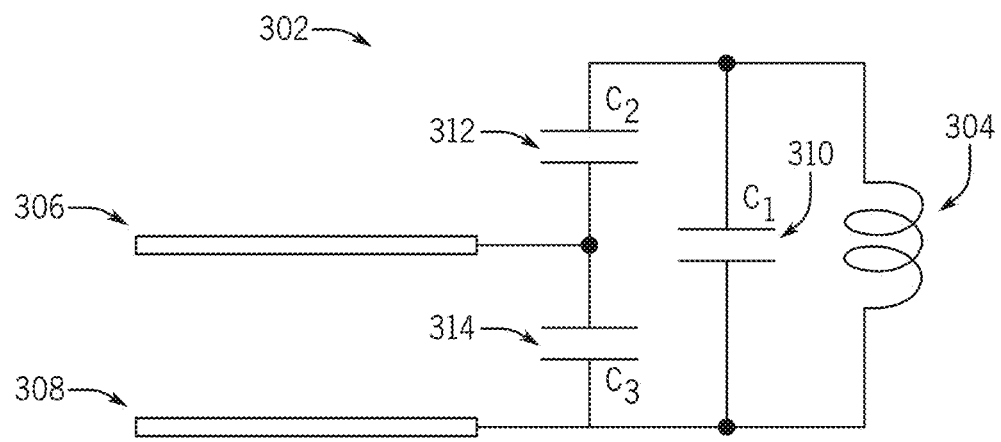
FIG. 3 shows an example of a circuit diagram of a circuit that can be used in the implementation of a wireless radio frequency lesioning circuit in accordance with some embodiments of the disclosed subject matter.

FIG. 3 shows an example of a circuit diagram of a circuit 302 that can be used in the implementation of a wireless radio frequency lesioning circuit in accordance with some embodiments of the disclosed subject matter. As shown in FIG. 3, circuit 302 can include a receiving coil 304, a pair of electrodes 306 and 308, and tuning capacitors 310, 312 and 314.

In some embodiments, receiving coil 304 can be implemented using a conductor(s) and/or dimensions suitable for implantation into a target area of the subject. For example, receiving coil 304 can be implemented as a two-turn coil using enameled copper wires. In a more particular example, each turn of receiving coil 304 can be implemented using thirty-six enameled copper wires that each has a 28 American Wire Gage (AWG) diameter connected in parallel to create a two-turn coil. In one particular implementation of such a coil, the measured winding resistance at 6.78 megahertz (MHz) was 50.5 mΩ. Note that examples described herein are generally described for an operating frequency of 6.78 MHz, as this is a frequency at which medical devices are often operated due to its inclusion in as a reserved industrial, scientific, and medial (ISM) radio band. However, this is merely an example, and the systems described herein can be configured to operate at many different frequencies based on principles described in the disclosed subject matter.

In some embodiments, circuit 302 can be tuned to a particular operating frequency with capacitors 310-314 (sometimes also referred to herein as capacitors $C_1$-$C_3$, respectively). In some embodiments, capacitor 312 and capacitor 314 can form a low-loss passive potential divider to adjust the electrode voltage. In one particular example, for a wireless receiver tuned to an operating frequency of 6.78 MHz, capacitors 310-314 can have values of 6 nanofarads (nF), 470 picofarads (pF), and 638 pF, respectively.

In some embodiments, as described below in connection with FIGS. 5A, 5B, 6A, and 6B, the components of circuit 302, including the electrodes, capacitors, and receiving coil can be integrated together, and implanted as a unit, which can eliminate the need for connecting components during an implantation procedure, potentially reducing the time, complexity, and cost of the implant surgery.

As shown in FIG. 3, a device implementing circuit 302 is powered by a wireless power transfer system using near magnetic field coupling (e.g., operating at 6.78 MHz, or any other suitable frequency). Accordingly, as the received voltage is already at in the RF range, no additional rectifier or RF signal generator are needed to drive electrodes 306 and 308.

Figure 4:
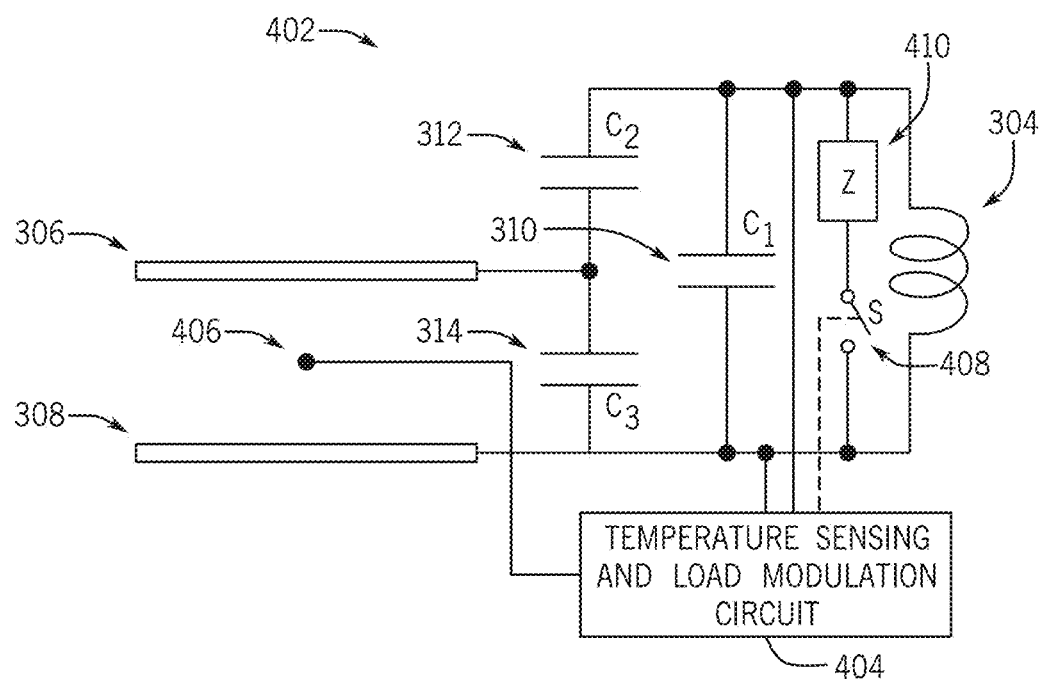
FIG. 4 shows an example of a circuit diagram of a circuit that can be used in the implementation of another wireless radio frequency lesioning circuit in accordance with some embodiments of the disclosed subject matter.

FIG. 4 shows an example of a circuit diagram of a circuit 402 that can be used in the implementation of another wireless radio frequency lesioning circuit in accordance with some embodiments of the disclosed subject matter.

As shown in FIG. 4, circuit 402 is similar to circuit 302 and includes receiving coil 304, electrodes 306 and 08, and capacitors 310-314. Additionally, in some embodiments, circuit 402 includes a temperature sensing and load modulation circuit 404 that can receive a signal from a temperature sensor 406 that is located near electrodes 306 and/or 308 to sense the temperature of tissue being treated. In some embodiments, temperature sensor 406 can output a signal to temperature sensing circuit 404, which can control operation of a switch 408 that is connected in series with a circuit element 410 with an impedance Z, and in parallel with receiving coil 304. In some embodiments, temperature sensing circuit 404 can be configured to close switch 408 when the temperature rises above a particular level (e.g., 55° C., 80° C., or any other suitable temperature).

In some embodiments, temperature sensor 406 and temperature sensing circuit 404 can be implemented using any suitable components. For example, temperature sensor 406 can be implemented using a thermocouple, a solid state temperature sensor, a thermistor, etc. In some embodiments, temperature sensing circuit 404 can be powered by receiving coil 304, eliminating any need for an additional antenna and/or driving circuit. Additionally, in some embodiments, temperature sensing circuit 404 can include one or more rectifiers to provide a DC voltage to one or more components of temperature sensing circuit 404. In some embodiments, temperature sensing circuit 404 can include one or more components to amplify the signal from temperature sensor 406, and use the signal to control the state of switch 408. Additionally or alternatively, in some embodiments, temperature sensing circuit 404 can include one or more components to amplify a voltage that controls switch 408 with a temperature dependent gain (e.g., by using a resister or thermistor to control the gain as the temperature changes). In some such embodiments, the amplifier circuit can act as a temperature sensor. In some embodiments, temperature sensing circuit 404 can include components to digitize the temperature signal, such as an analog-to-digital converter. In some embodiments, switch 408 and/or component 410 can be a component that has an impedance that changes (e.g., an increase or decrease in the real and/or imaginary component of the impedance) with temperature, but that is relatively stable below a threshold temperature (e.g., 55° C., 80° C., or any other suitable temperature) such that circuit 402 becomes detuned from the operating frequency.

In some embodiments, circuit element 410 can be a capacitor or a resistor, such as the internal resistance of switch 408. When switch 408 is closed, the addition of the impedance of circuit element 410 will detune receiving coil 304, and alter the input impedance of the transmitting coil. In some embodiments, the transmitting coil impedance can be measured and demodulated in real-time, and used to calculate the tissue temperature.

FIGS. 5A and 5B show an example 502 of a wireless radio frequency lesioning device in accordance with some embodiments of the disclosed subject matter. As shown in FIG. 5A, a receiving coil 504 can be electronically connected to electrodes 506 and 508 and resonant capacitors 510 (e.g., capacitors 310-314). In some embodiments, receiving coil 504 can be implemented with dimensions suitable for implantation near tissue that is to be ablated. For example, receiving coil 504 can have a height H of about 5.5 millimeters (mm), an interior diameter of about 18 mm, and an exterior diameter D of about 24 mm.

In some embodiments, electrodes 506 and 508 can be implemented with an exposed length L and a separation W suitable to create a lesioned tissue footprint of a desired volume. For example, larger values of L and W may generate larger footprints, and thus necessitate less precise placement, but may also require more power to heat the entire volume of the footprint to at least a particular temperature and/or may cause collateral damage to surrounding tissue that is not targeted for lesioning. Smaller values of L and W, by contrast, may generate a more focused footprint, and thus may require less power to heat the entire volume of the footprint to at least a particular temperature and/or may cause less collateral damage to surrounding tissue that is not targeted for lesioning, but may necessitate more precise placement during implantation surgery to insure that the targeted tissue is within the device's footprint. In one particular example, the exposed length of electrodes 506 and 508 can be about 8 mm, and the separation can be about 5 mm.

As shown in FIG. 5B, when implanted, electrodes 506 and 508 can be separated by a conductive medium 522 (e.g., muscle tissue) that provides a path for current to flow between electrode 506 and electrode 508. Additionally, in some embodiments, an insulating coating 524 can be placed on at least a portion of electrodes 506 and 508 to create a more focused zone through which current will flow (e.g., causing more intense heating in a smaller zone for a given input power). In the example shown in FIGS. 5A and 5B, electrodes 506 and 508 are each a length of AWG 20 wire, but this is merely an example, and any suitable conductor can be used that can support the power generated by the receiving coil. Although not shown, various other electrode shapes can be used to produce heat in different patterns (e.g., by causing the current to flow in a different pattern through the subject's tissue).

Figure 2:
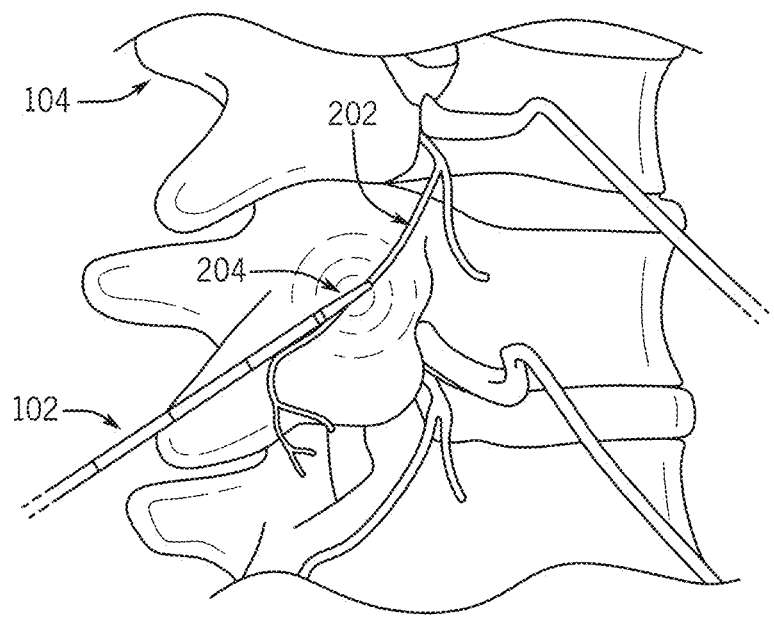
FIG. 2 shows an example of a portion of the conventional radio frequency lesioning system of FIG. 1.

FIG. 6A1 shows an example 602 of another wireless radio frequency lesioning device in accordance with some embodiments of the disclosed subject matter, and FIG. 6A2 shows an example cross-sectional schematic diagram of the wireless radio frequency lesioning device of FIG. 6A1 in accordance with some embodiments of the disclosed subject matter. As shown in FIGS. 6A1 and 6A2, device 602 can include a receiving coil 604 with electrodes portions 606 and 608 positioned at either end of coil 604, and resonant capacitors 610 (e.g., capacitors 310, 312, and 314) positioned within receiving coil 604 and between electrode portions 606 and 608. As described below in connection with FIGS. 6C1-6C12, electrodes of various shapes can be positioned at electrode portion(s) 606 and/or 608. Additionally, in some embodiments, electrodes in the form of pads, relatively flat contacts, or loops can be positioned at electrode portion(s) 606 and/or 608 in an arrangement that does not significantly impair power coupling between the transmitter and the receiving coil.

FIG. 6B1 shows an example 612 of yet another wireless radio frequency lesioning device in accordance with some embodiments of the disclosed subject matter, and FIG. 6B2 shows an example cross-sectional schematic diagram of the wireless radio frequency lesioning device of FIG. 6B1 in accordance with some embodiments of the disclosed subject matter. As shown in FIGS. 6B1 and 6B2, the exterior of device 612 can have a pill or capsule shape (e.g., a generally cylindrical shape with hemispherical ends), and can include a receiving coil 614 with electrode portions 616 and 618 positioned at any suitable position on the exterior of the capsule, such as the sides (as shown), the ends, on multiple sides, around the circumference of the capsule body, etc. As shown, resonant capacitors 620 (e.g., capacitors 310, 312, and 314) can be positioned within receiving coil 614. Additionally or alternatively, in some embodiments, resonant capacitors 620 can be disposed within the capsule body of device 612 at any suitable position, and in some cases can be disposed outside of the capsule body, or formed integrally within the capsule body. As described below in connection with FIGS. 6C1-6C12, electrodes of various shapes can be positioned at electrode portion(s) 616 and/or 618. Additionally, in some embodiments, electrodes in the form of pads or relatively flat contacts can be positioned at electrode portion (s) 616 and/or 618 in an arrangement that does not significantly impair power coupling between the transmitter and the receiving coil. Note that, although not shown, a receiving coil (e.g., receiving coil 504, 604, and/or 614) can be configured to surround a core material.

Figure 12:
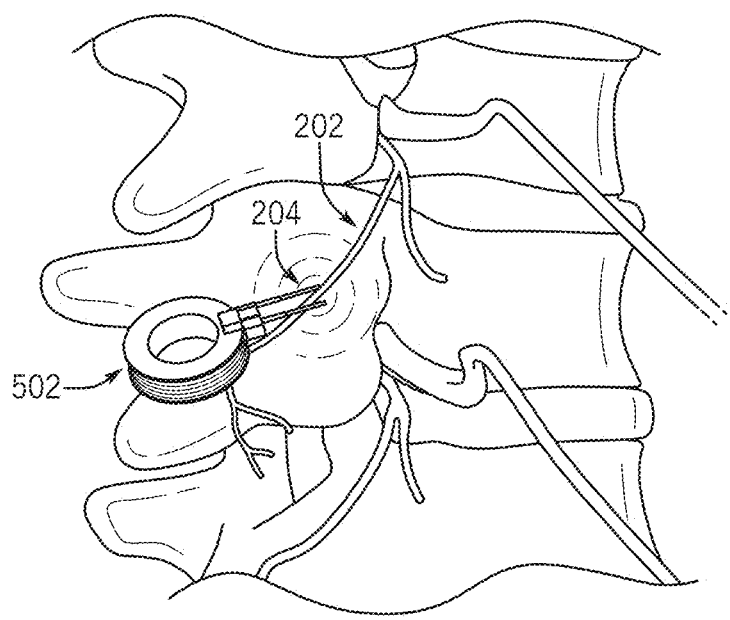

FIGS. 6C1 to 6C12 show various example electrode shapes that can be used in connection with device 602 and/or 612 in accordance with some embodiments of the disclosed subject matter. For example, as shown in FIGS. 6C1 to 6C12, an electrode portion 626 can include one or more electrodes 622 of various shapes. Note that, embodiments with multiple electrodes within the same electrode portion 626 can be connected in parallel. Note that although various electrodes shapes are shown, these are merely examples, and electrodes of any suitable shape can be used that, when positioned relative to the receiving coil, do not significantly impair power coupling between the transmitter and the receiving coil. For example, power coupling may be negatively impacted by an electrode that forms a conductive loop or solid conductive plate that overlaps the end of the receiving coil, with the extent of the decoupling based on the area and/or materials used for the electrode. In some embodiments, although electrodes 622 appear relatively flat, electrodes can have a raised and/or variable profile, which can, in some cases, include spikes or other protrusions. As described above in connection with FIGS. 6A1, 6A2, 6B1, 6B2, and 6C1 to 6C8, electrodes of many shapes can be used, and the shapes described herein are not intended to form an exhaustive list of all possible electrode shapes that can be used in connection with the mechanisms described herein.

Figure 7A:
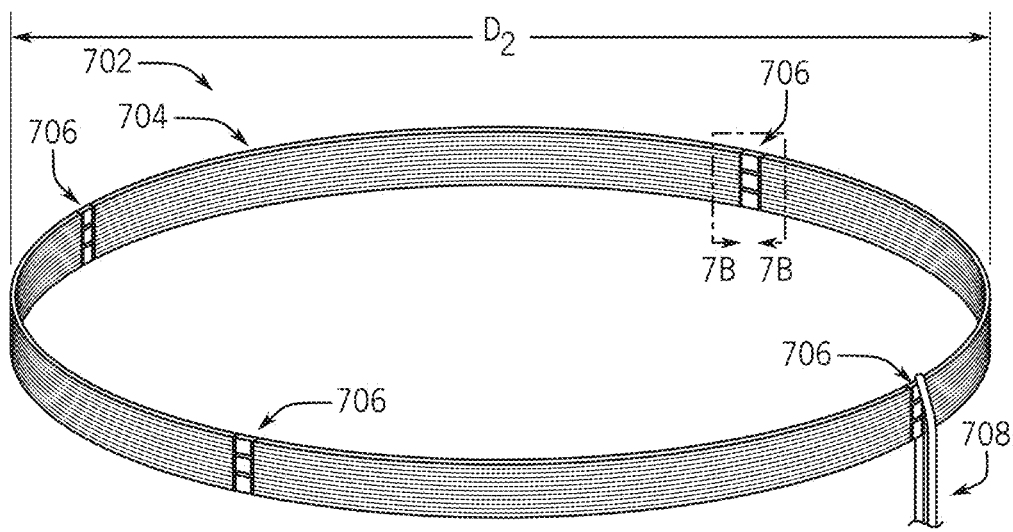
FIG. 7A shows an example of a wireless radio frequency transmitting coil in accordance with some embodiments of the disclosed subject matter.

FIG. 7A shows an example 702 of a wireless radio frequency transmitter in accordance with some embodiments of the disclosed subject matter. In some embodiments, transmitting coil 702 can include a single transmitting coil 704 with segments separated by resonant capacitors 706, and can be electrically connected to an RF signal generator by wires 708. In some embodiments, a diameter $D_2$ of transmitting coil 704 can be configured based on the part(s) of a subject that are to be placed within or near transmitting coil 704. For example, in one example, transmitting coil 704 can be implemented for use as a transmitter configured as a device which can be positioned near a known location of the implanted device. Note that a single-coil configuration shown in FIG. 7A is generally appropriate when the implanted device is not deep within the subject's body and where the location of the implanted device is sufficiently known such that the single transmitting coil 704 can be positioned to ensure that the device is within a predetermined distance of the plane of the single transmitting coil 704. In some embodiments, transmitting coil 704 can be implemented with any suitable number of turns. In one particular example, transmitting coil 704 can have 3 turns, and each turn can be made of twelve 18 AWG enameled copper wires connected in parallel.

Figure 7B:
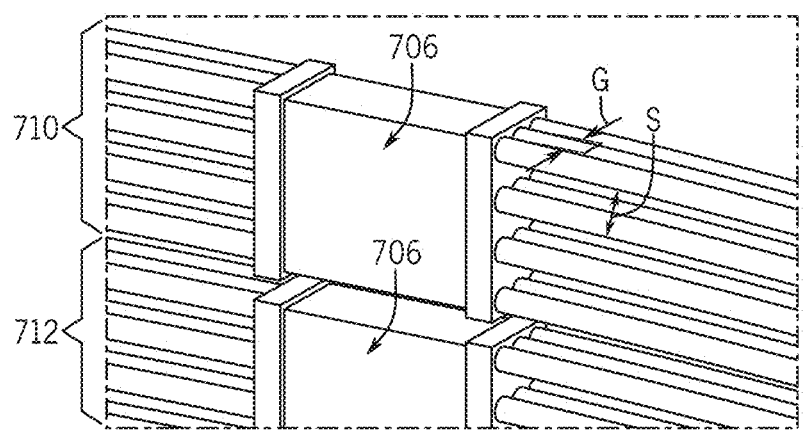
FIG. 7B shows an example of a portion of the wireless radio frequency transmitting coil of FIG. 7A in accordance with some embodiments of the disclosed subject matter.

FIG. 7B shows an example of a portion of the wireless radio frequency transmitting coil of FIG. 7A in accordance with some embodiments of the disclosed subject matter. As shown in FIG. 7B, the wires in an individual turn (710, 712) can be grouped into layers (e.g., of three wires each). Wires within a single layer can be separated by a gap G, and the layers can be separated by a distance S from another layer in the same turn. In one particular example, using twelve 18 AWG wires per turn G can be about 1.3 mm, and S can be about 2 mm.

Figure 7C:
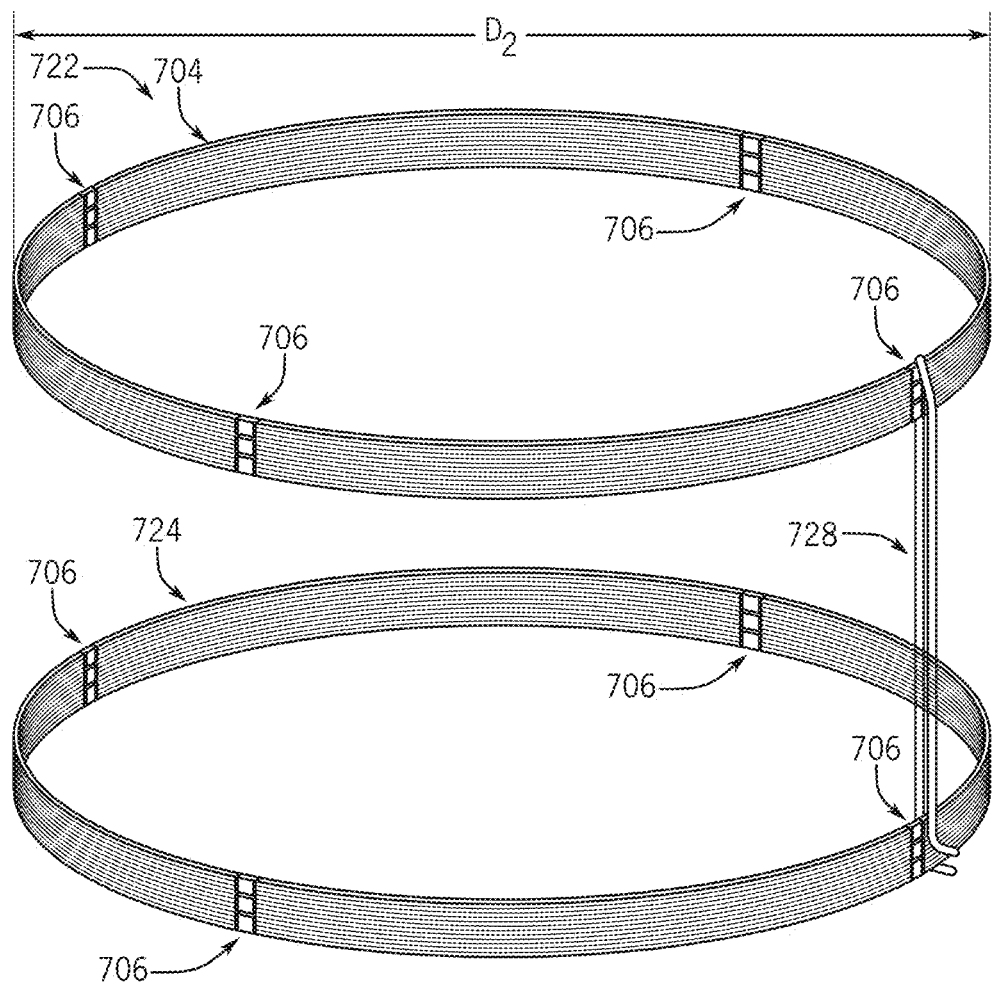
FIG. 7C shows an example of another wireless radio frequency transmitting coil in accordance with some embodiments of the disclosed subject matter.

FIG. 7C shows an example 722 of another wireless radio frequency transmitter implemented as a Helmholtz coil in accordance with some embodiments of the disclosed subject matter. In some embodiments, transmitting coil 722 can include two transmitting coils 704 and 724 separated by a distance H, and both transmitting coils 704 and 724 can be connected to an RF signal generator by wires 728. In some embodiments, transmitter 722 can be configured to surround a subject's body (e.g., the subject's torso can be placed within transmitting coils 704 and 722, or the subject's torso can be placed between transmitting coils 704 and 722,) to generate a uniform magnetic field in the subject's body. As another example, transmitter 722 can be implemented with a smaller diameter for use as a transmitter for powering an implant within a subject's limb by surrounding the subject's limb to generate a uniform magnetic field within the limb. In one particular example, transmitter 722 can be implemented as a Helmholtz coil transmitter with a diameter $D_2$ of about 40 centimeters. In some embodiments, coils 704 and 724 can each include 3 turns, that are each made of twelve 18 AWG enameled copper wires connected in parallel.

Although a Helmholtz coil-type transmitter can provide a uniform magnetic field in a large volume so that the receiver can be located deep in the body without precise alignment, the excitation voltage required to do so may be excessively high. For example, a 40-cm Helmholtz coil implemented with 3 turns per coil, with each turn including twelve 18 AWG enameled copper wires connected in parallel (without resonant capacitors) has a coil inductance of 17.6 microhenries (µH). Exciting such a transmitter with a current $I_t=1.5$ $A_{rms}$, the excitation voltage of the transmitter is $V_t=2\pi f L I_t=1.1$ $kV_{rms}$, which present cause safety issues and substantially increase the manufacturing cost (e.g., due to the requirement to use components configured to work at high voltage). In some embodiments, by segmenting the transmitting coil with resonant capacitors (e.g., as described in Tang U.S. Patent Application Publication No. 2015/0244178, which is hereby incorporated by reference herein in its entirety), the transmitting coil voltage can be significantly reduced to a safe level. As shown in FIGS. 7A-7C, each turn of the coil can be divided into four segments by resonant capacitors 706, resulting in a total of 24 capacitors and 24 segments. In some embodiments, the transmitter (e.g., transmitter 702 or 722) can be tuned to 6.78 MHz using 24 765-pF capacitors inserted evenly over the coil. In some such embodiments, when the transmitter is operated at the resonant frequency, the voltage across each segment can be cancelled by the adjacent capacitor voltage, facilitating a very low excitation voltage, which is proportional to the coil resistance.

In one particular example, the impedance of a transmitter configured as a Helmholtz coil with two coils that were each implemented with 3 turns per coil, with each turn including twelve 18 AWG with 24 765-pF resonant capacitors and 24 total segments (i.e., 12 resonant capacitors and 12 segments per coil) was calculated using the segmented coil model described in Tang U.S. Patent Application Publication No. 2015/0244178. The calculated and measured impedances were consistent, as described below in connection with FIG. 13.

Figure 8:
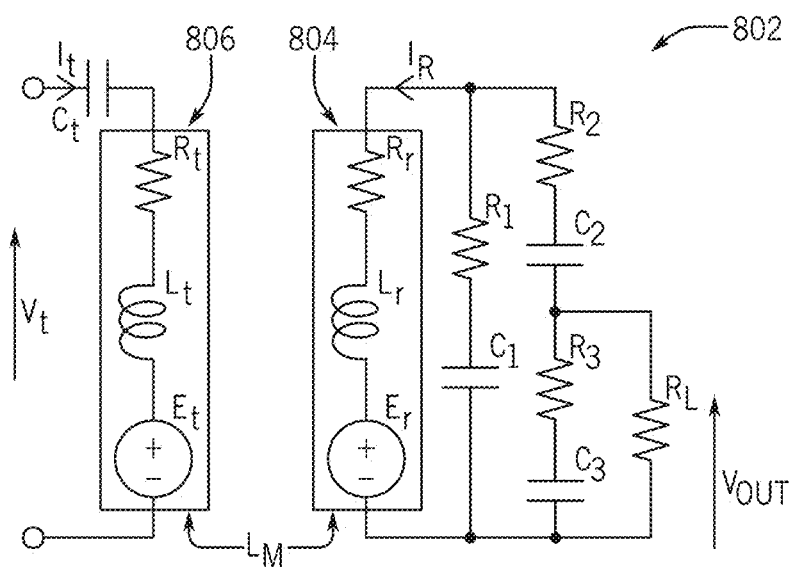
FIG. 8 shows an example of a circuit model of a wireless radio frequency lesioning system in accordance with some embodiments of the disclosed subject matter.

FIG. 8 shows an example 802 of a circuit model of a wireless radio frequency lesioning system in accordance with some embodiments of the disclosed subject matter. As shown in FIG. 8, system 802 can modeled as a circuit that includes a receiving coil 804 and a paired transmitting coil 806, in which inductance of transmitting coil 806 is denoted as $L_t$. The series resistance of the transmitting coil winding and the segment capacitors is denoted as $R_t$, and the segment capacitors (e.g., resonant capacitors 706) can be considered to be in series and can be represented by a lumped capacitance $C_t$. In circuit model 802, the resistance and inductance of receiving coil 804 can be represented by a resistance $R_r$ and inductance $L_r$, respectively, and capacitances of the resonant capacitors of the receiver (e.g., capacitors 310-314) denoted as $C_1$ to $C_3$ can be modeled with an equivalent series resistance (ESR) $R_1$ to $R_3$, respectively. In general, when the electrodes are fully inserted into muscle tissue, the imaginary part of the impedance across the electrodes was negligible, and the load of the energy coupling system can be represented by a resistor $R_L$, shown in FIG. 8. The induced voltage at the transmitting and receiving coils caused by mutual coupling can be represented as $$E_t = j\omega L_m I_r, \tag{1}$$

$$E_r = j\omega L_m I_t, \tag{2}$$

where $\omega=2\pi f$, f is the operating frequency, $I_t$ and $I_r$ are the currents of the transmitting and receiving coils, respectively, and $L_m$ is the mutual inductance.

Using loop analysis, the output power, $P_L$, and efficiency, $\eta$, of the system can be represented as $$P_L = \left| \frac{Z_{C1} E_r}{(Z_{C1} Z_r + Z_r Z_{C2} + Z_{C1} Z_{C2})\left(\frac{R_L + Z_{C3}}{Z_{C3}}\right) + (Z_r + Z_{C1}) R_L} \right|^2 R_L, \tag{3}$$

and $$\eta = \frac{P_L}{P_L + P_t + P_r}, \tag{4}$$

where $Z_{C1} = R_1 + \frac{1}{j\omega C_1}$, $Z_{C2} = R_2 + \frac{1}{j\omega C_2}$, $Z_{C1} = R_3 + \frac{1}{j\omega C_3}$, $Z_r + R_r + j\omega L_r$, $P_t$ where $Z_{C1} = R_1 + \frac{1}{j\omega C_1}$, $Z_{C2} = R_2 + \frac{1}{j\omega C_2}$, $Z_{C1} = R_3 + \frac{1}{j\omega C_3}$, $Z_r = R_r + j\omega L_r$, $P_t$ and $P_r$ are the power losses of the transmitting and receiving coils, respectively can be represented as $$P_t = I_t^2 R_t, \tag{5}$$

$$P_r = \left| \frac{[(Z_{C1} + Z_{C2})(R_L + Z_{C3}) + R_L Z_{C3}] E_r}{(Z_{C1} Z_r + Z_r Z_{C2} + Z_{C1} Z_{C2})(R_L + Z_{C3}) + (Z_r + Z_{C1}) Z_{C3} R_L} \right|^2 R_r, \tag{6}$$

Figure 9:
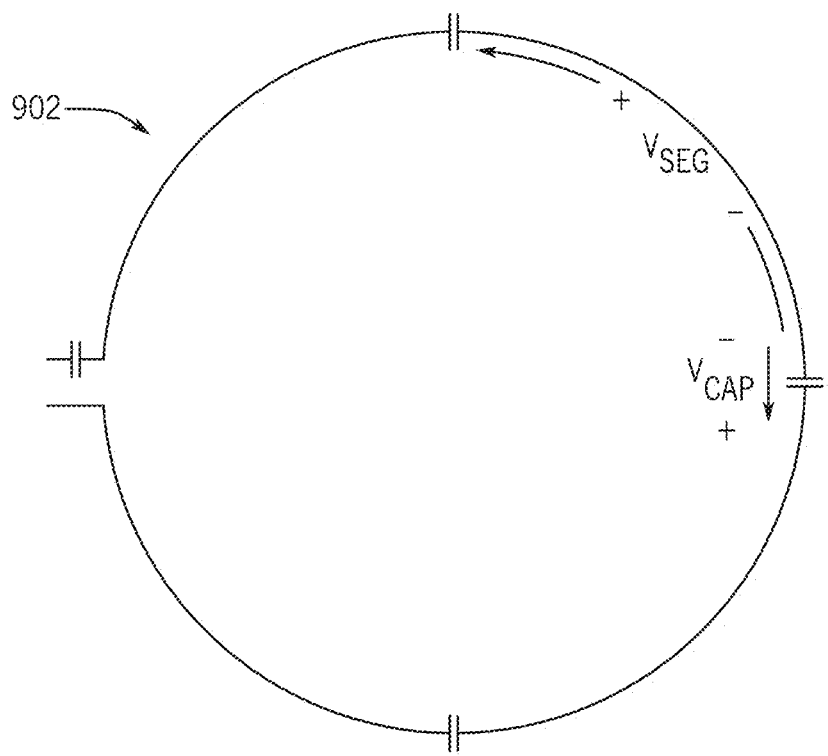
FIG. 9 shows an example of a diagram of coil segmentation using resonant capacitors in accordance with some embodiments of the disclosed subject matter.

FIG. 9 shows an example 902 of a diagram of coil segmentation using resonant capacitors in accordance with some embodiments of the disclosed subject matter. As shown in FIG. 9, transmission coil 902 is divided into segments using series capacitors (e.g., capacitors 706 described above in connection with FIGS. 7A to 7C), where the series capacitors can be physically located along the length of the transmitting coil to segment the transmitting coil into a desired number of coil segments (e.g., four segments per turn in the implementation described above in connection with FIGS. 7A-7C). The series capacitors can be sized to provide a transmission coil resonance frequency that is equal to the desired operating frequency of the wireless magnetic power transmission system (e.g., 6.78 MHz). By placing the series capacitors along the transmission coil, the voltage of each coil segment can be substantially canceled out by the corresponding series capacitor when the transmission coil resonant frequency is equal to the system operating frequency as the voltage across each of the series capacitors is equal and in opposite polarity to the voltage across the coil segments. Any residual voltage present on the coil segments can be the result of the series resistance of the coil segment conductors. Additionally, this can result in the transmission coil segment excitation voltage being equal to the total transmission coil excitation voltage, divided by the total number of transmission coil segments. Furthermore, by operating the transmission coil at the resonant frequency, the impedance of the coil can be minimized and can approximately equal the transmission coil resistance. In one particular example, the transmission coil resistance was less than five Ohms.

Figure 10:
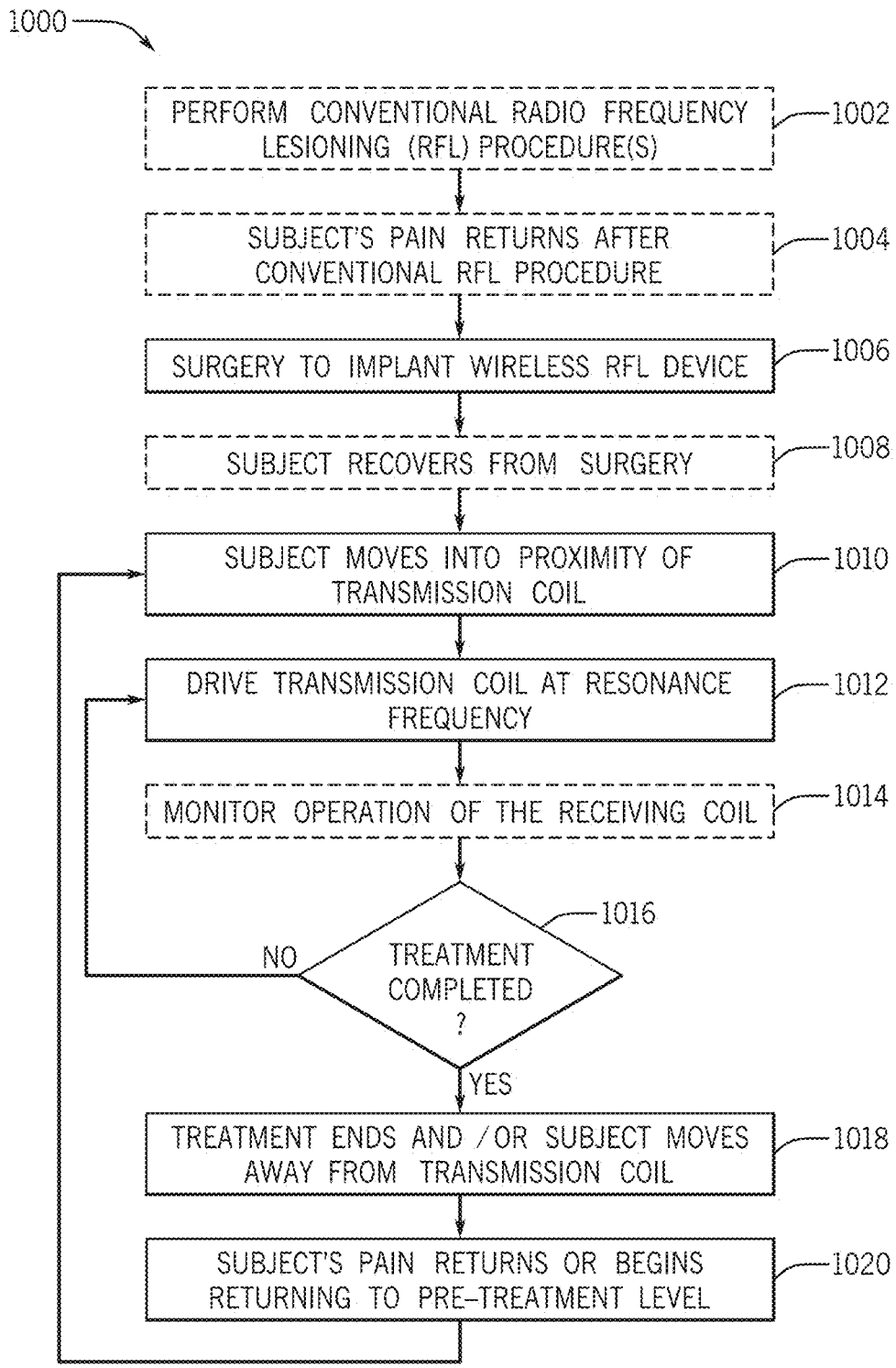
FIG. 10 shows an example of a process for treating a subject using a wireless radio frequency lesioning system in accordance with some embodiments of the disclosed subject matter.

FIG. 10 shows an example 1000 of a process for treating a subject using a wireless radio frequency lesioning system in accordance with some embodiments of the disclosed subject matter. As shown in FIG. 10, at 1002, process 1000 can optionally begin by performing one or more conventional RFL procedures on a subject. For example, before implanting a wireless RFL device, a conventional RFL procedure can be performed to determine whether the procedure relieves the subject's pain.

At 1004, process 1000 can optically include the subject reporting that pain that was relieved by the conventional RFL procedure has begun to return. Note that, in some cases, a conventional RFL procedure may permanently relieve pain for some subjects, in which case an implantable device may not be necessary.

At 1006, process 1000 can include performing a surgical procedure to implant a wireless RFL device implemented in accordance with some embodiments of the disclosed subject matter. In some embodiments, such a surgery can be superficially similar to a conventional RFL procedure, as it can include locating a position at which RFL is to be performed using images generated using an X-ray scanner, such as a fluoroscopy guided procedure. In some embodiments, any suitable technique or combination of techniques can be used to position the wireless RFL device. For example, the wireless RFL device can be introduced using a large needle and/or catheter which can be guided into position based on bone landmarks in the X-ray images.

At 1008, process 1000 can optionally include a recovery period 1008 during which the subject recovers from the surgical procedure prior to energizing the implanted wireless RFL device.

At 1010, process 1000 can include moving the subject into proximity of a transmitter that generates a magnetic field at the resonant frequency of the implanted wireless RFL device. As described above in connection with FIGS. 7A-7C, the transmitted can be a single coil transmitter (e.g., where the implanted wireless RFL device can be reliably located and is positioned relatively close to the surface of the subject's body) or a double coil Helmholtz transmitter. In some embodiments, the transmitter can be located at a clinical facility (e.g., a hospital, an outpatient clinic, etc.), or at another location (e.g., the subject's home).

At 1012, process 1000 can include driving the transmitter at the resonance frequency of the implanted wireless RFL device when it has been brought into position. For example, as described above, a 6.78 MHz signal can be applied to the transmitter from a RF generator.

At 1014, process 1000 can optionally include monitoring operation of the receiving coil. For example, as described above in connection with FIG. 4, a receiving coil that is configured with a temperature sensing circuit can detune the receiving coil when a particular temperature is reached (e.g., 42° C., 55° C., 80° C.), and process 1000 can include measuring the coil impedance of the transmitter, and using the coil impedance to determine operation of the wireless RFL device (e.g., by calculating whether the temperature has reached a particular threshold based on the relationship of the coil impedance to the impedance of the wireless RFL device).

At 1016, process 1000 can include determining whether the treatment being provided has been completed. For example, if the transmitted is configured to determine whether a particular temperature threshold has been reached, process 1000 can include determining that a treatment has been completed when the threshold temperature has been reached. As another example, in some embodiments, process 1000 can include measuring the amount of time for which the transmitter has been providing power to a particular implanted device, and can cease operation after a particular period of time has elapsed. In such an example, process 1000 can determine that a treatment has been completed when a predetermined amount of time has elapsed. As yet another example, in some embodiments, process 1000 can use multiple criteria to determine whether a treatment has been completed. In a more particular example, process 1000 can include determining whether a particular temperature threshold has been reached or whether a particular amount of time has elapsed. If the treatment has not been completed ("NO" at 1016), process 1000 can return to 1012, and the transmitter can continue to be provided with the RF signal. Otherwise, if the treatment has been completed ("YES" at 1016), process 1000 can move to 1018.

As described below (e.g., in connection with FIG. 18), a wireless RFL device implemented in accordance with some embodiments of the disclosed subject matter that is powered by near magnetic field coupling can lesion biological tissue with a temperature of more than 80° C., while being smaller than many battery-operated implanted spinal cord stimulation devices. For example, a wireless RFL device with a 2.4-cm diameter receiver is smaller than many commercially available implantable devices, having a footprint area that is less than 20% of many spinal cord stimulators. Note that the receiver diameter can be adjusted based on the desired lesioning temperature. For example, because many biological tissues can be considered lesioned at 55° C., a wireless RFL device to achieve such a temperature can require less power, and consequently can be configured to have a smaller diameter receiving coil.

Note that, although RFL is generally described herein as including applying continuous RF power, devices implemented in accordance with some embodiments of the disclosed subject matter can be used to deliver treatment based on other treatment modalities. For example, in some cases, pain-signaling nerves can be successfully treated with temperatures that are significantly lower than a temperature at which tissue is generally considered lesioned (e.g., at 42° C. rather than upwards of 55° C.) by using pulsed RFL techniques (e.g., as described in Liliang et al. "Pulsed radiofrequency lesioning of the suprascapular nerve for chronic shoulder pain: a preliminary report," Pain Medicine, Vol. 10, No. 1, January-February 2009, pp. 70-75; Navani et al. "A Case of Pulsed Radiofrequency Lesioning for Occipital Neuralgia," Pain Medicine, Vol. 7, No. 5, October 2006, pp. 453-456; and Shanthanna et al. "Assessing the Effectiveness of 'Pulse Radiofrequency Treatment of Dorsal Root Ganglion' in Patients with Chronic Lumbar Radicular Pain: Study Protocol for a Randomized Control Trial," Trials, Vol. 13, No. 52, April 2012; each of the preceding references is hereby incorporated by reference herein in its entirety). In some such embodiments, in which pulsed RFL is used to treat pain, a wireless RFL device can potentially include a yet smaller receiving coil as the instantaneous power required to perform pulsed RFL may be lower than the power required to perform traditional RFL using a wireless RFL device. Note that, although pulsed RFL may rely on a different mechanism to cause a therapeutic (i.e., the therapeutic effect is not necessarily due to tissue destruction), pulsed RFL is sometimes referred to as a lesioning, and devices that can be used to provide an RFL treatment can also be used to provide pulsed RFL treatments (e.g., using a different RF signal generator, using an RF signal generator in a different mode, etc.).

At 1018, process 1000 can include ending the treatment (e.g., by a processor controlling administration of the treatment) and/or the subject moving away from the transmission coil, which can remove the implanted wireless RFL device from the range of the transmitter, thereby halting any treatment that was in progress.

At 1020, process 1000 can include a subject's pain beginning to return to a pre-treatment level after a period of time has passed since a successful RFL procedure (e.g., several months after the treatment) at 1010-1018. In some embodiments, when the subject's pain begins returning at 1020, process 1000 can return to 1010 to begin another treatment.

Figure 11:
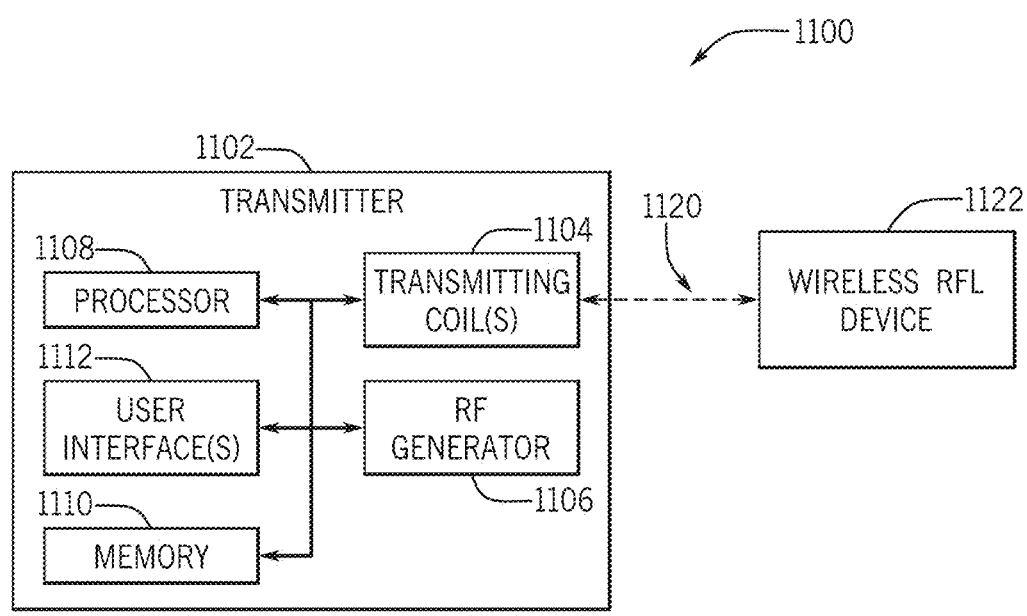
FIG. 11 shows an example of hardware that can be used to implement at least a portion of a wireless radio frequency lesioning system in accordance with some embodiments of the disclosed subject matter.

FIG. 11 shows an example of hardware 1100 that can be used to implement at least a portion of a wireless radio frequency lesioning system in accordance with some embodiments of the disclosed subject matter. For example, system 1100 can include a transmitter 1102 (e.g., transmitted 702 or 722) that is linked via a wireless power link 1120 to a wireless RFL device 1122 (e.g., wireless RFL device 502 or 602). As shown in FIG. 11, in some embodiments, transmitter 1102 can include a transmitting coil or coils 1104, a radiofrequency generator 1106 for providing an RF signal to transmitting coil(s) 1104, a processor 1108, memory 1110, and/or a user interface 1112. In some embodiments, transmitting coil(s) can be implemented using any suitable technique or combination of techniques, such as those described above in connection with FIGS. 7A-7C and 8. In some embodiments, RF generator 1106 can be any suitable RF generator for providing an RF signal of sufficient power at a particular RF frequency (e.g., 6.78 MHz) to facilitate power being transferred to implanted wireless RFL device 1122 from transmitting coil(s) 1104 via wireless power link 1120.

In some embodiments, processor 1108 can be any suitable hardware processor or combination of processors, such as a central processing unit (CPU), a graphics processing unit (GPU), etc. In some embodiments, user interface 1112 can include can include any suitable display device(s) (e.g., a monitor, a built-in display, a wireless display such as a display of a smartphone or tablet computer, etc.), and/or user input devices (e.g., a mouse, a keyboard, a touchscreen, a microphone, etc.).

In some embodiments, memory 1110 can include any suitable storage device or devices that can be used to store instructions, values, etc., that can be used, for example, by processor 1108 to present information and/or receive user input using user interface 1112, to control operation of RF generator 1106, to receive signals from transmitting coil(s) 1104 (e.g., to measure impedance, etc.). Memory 1110 can include any suitable volatile memory, non-volatile memory, storage, any other suitable type of storage medium, or any suitable combination thereof. For example, memory 1110 can include RAM, ROM, EEPROM, one or more flash drives, one or more hard disks, one or more solid state drives, one or more optical drives, etc. In some embodiments, memory 1110 can have encoded thereon a computer program for controlling operation of transmitter 1102 and/or system 1100. In some such embodiments, processor 1108 can execute at least a portion of the computer program to control power to RF generator 1106 to provide treatment to a subject in which wireless RFL device 1122 has been implanted.

FIG. 12 shows an example of an implanted wireless radio frequency lesioning device in accordance with some embodiments of the disclosed subject matter. As shown in FIG. 12, wireless RFL device 502 can be implanted near a nerve 202 to wirelessly generate heat 204 to lesion nerve 202 during a RFL treatment.

Figure 13:
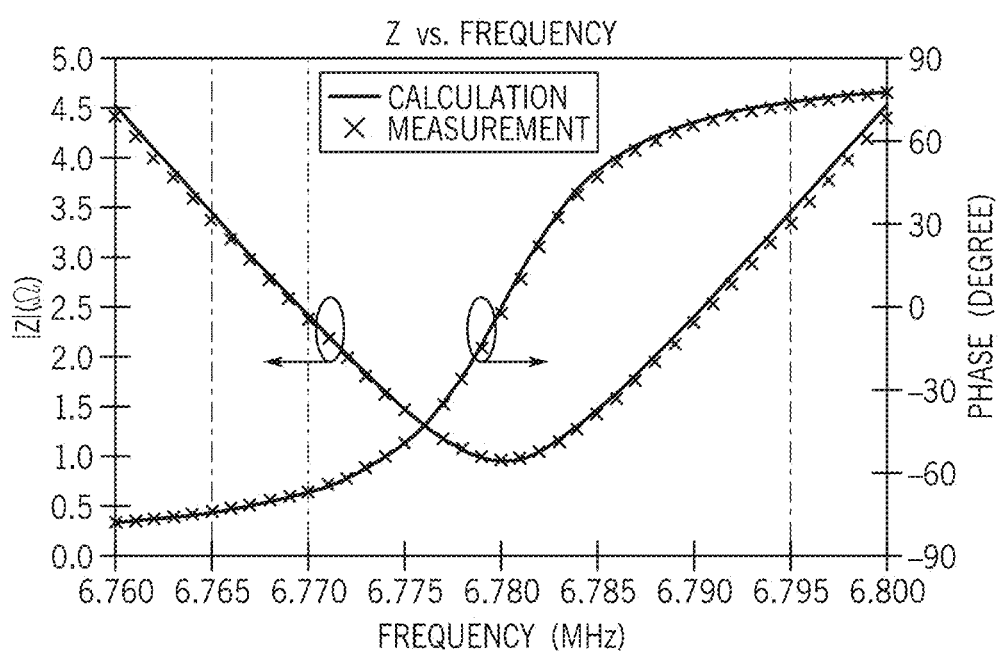
FIG. 13 shows a chart illustrating magnitude and phase of the impendence of a radio frequency transmitter implemented in accordance with some embodiments of the disclosed subject matter.

FIG. 13 shows a chart illustrating magnitude and phase of the impendence of a radio frequency transmitter implemented in accordance with some embodiments of the disclosed subject matter. In one particular example, the impedance and phase difference of a Helmholtz coil with two coils that were each implemented with 3 turns per coil, with each turn including twelve 18 AWG with 24 765-pF resonant capacitors and 24 total segments (i.e., 12 resonant capacitors and 12 segments per coil) using the segmented coil model described in Tang U.S. Patent Application Publication No. 2015/0244178 was calculated and measured. As shown in FIG. 13, the calculated and measured impedances were consistent. The measured coil resistance, including the ESR of the segment capacitors, is 0.97Ω at 6.78 MHz. In this example implementation, an excitation current of 1.6 $A_{rms}$ caused an excitation voltage of 1.55 $V_{rms}$ in the coils, which is much lower than the unsegmented counterpart (i.e., 1.1 $kV_{rms}$). In general, the segment voltage is equal to the unsegmented coil voltage divided by the number of segments, and accordingly, in the example implementation with 24 segments, the segment voltage is 46.9 $V_{rms}$.

Figure 14A:
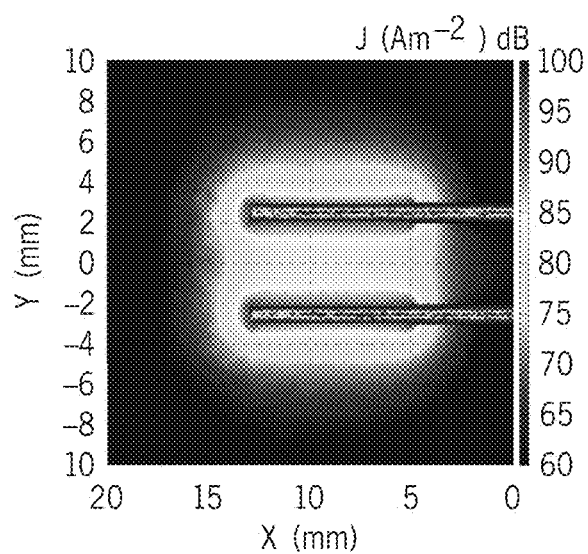
FIG. 14A shows a current density pattern on the x-y plane at z=0 calculated based on a three dimensional finite elements analysis simulation of electrodes of a wireless radio frequency lesioning device implemented in accordance with some embodiments of the disclosed subject matter.
Figure 14B:
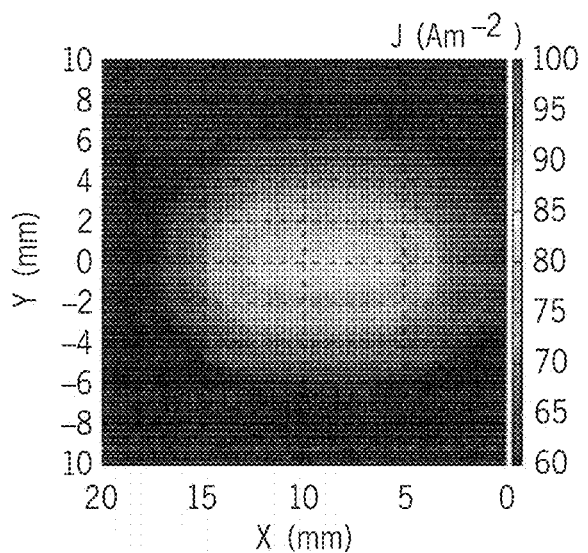
FIG. 14B shows a current density pattern on the x-z plane at y=0 calculated based on a three dimensional finite elements analysis simulation of electrodes of a wireless radio frequency lesioning device implemented in accordance with some embodiments of the disclosed subject matter.
Figure 14C:
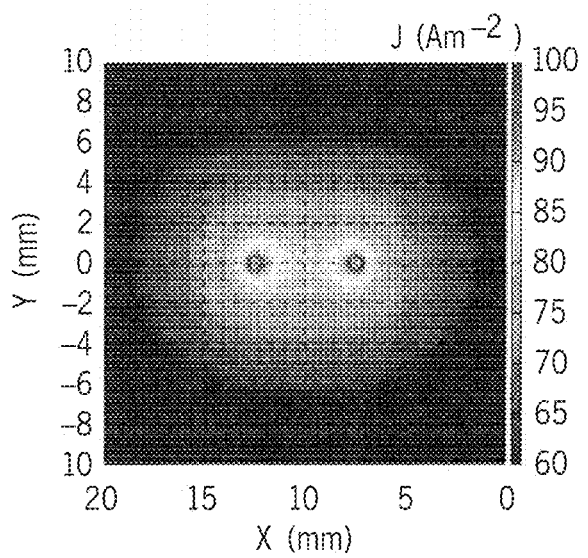
FIG. 14C shows a current density pattern on the y-z plane at x=4 mm from the electrode tips calculated based on a three dimensional finite elements analysis simulation of electrodes of a wireless radio frequency lesioning device implemented in accordance with some embodiments of the disclosed subject matter.

FIGS. 14A-14C show a current density pattern on the x-y plane at z=0, on the x-z plane at y=0, and on the y-z plane at x=4 mm, respectively, calculated based on a three dimensional finite elements analysis simulation of electrodes of a wireless radio frequency lesioning device implemented in accordance with some embodiments of the disclosed subject matter. A three-dimensional finite-element analysis (FEA) simulation was performed using Maxwell simulation software available from Ansys (of Canonsburg, Pa.) to simulate the current distribution, and thus the shape of muscle tissue lesioned by the bipolar RFL electrodes described above in connection with FIGS. 5A and 5B. In the simulation model (e.g., implemented as shown in FIG. 5B), the electrodes were surrounded by a conductive medium that simulated the electrical properties of human muscle tissue. FIGS. 14A-14C show the simulated current density patterns on three orthogonal planes around the electrodes, which indicates that the current density concentrates around and between the two electrodes. Since the power dissipation and tissue temperature are proportional to the current density, the simulated current density profiles are predictive of the shape of the lesioned region. Experimental results with chicken breast tissue lesioned by the bipolar RFL electrodes showed a lesioned area that was similar to the simulated results. Unlike the monopolar system used in convention RFL (e.g., as described in connection with FIG. 1), which usually generates spherically-shaped lesions, a bipolar electrode configuration can create lesions with different shapes for specific applications by changing the dimensions and orientations of the electrodes.

Figure 15:
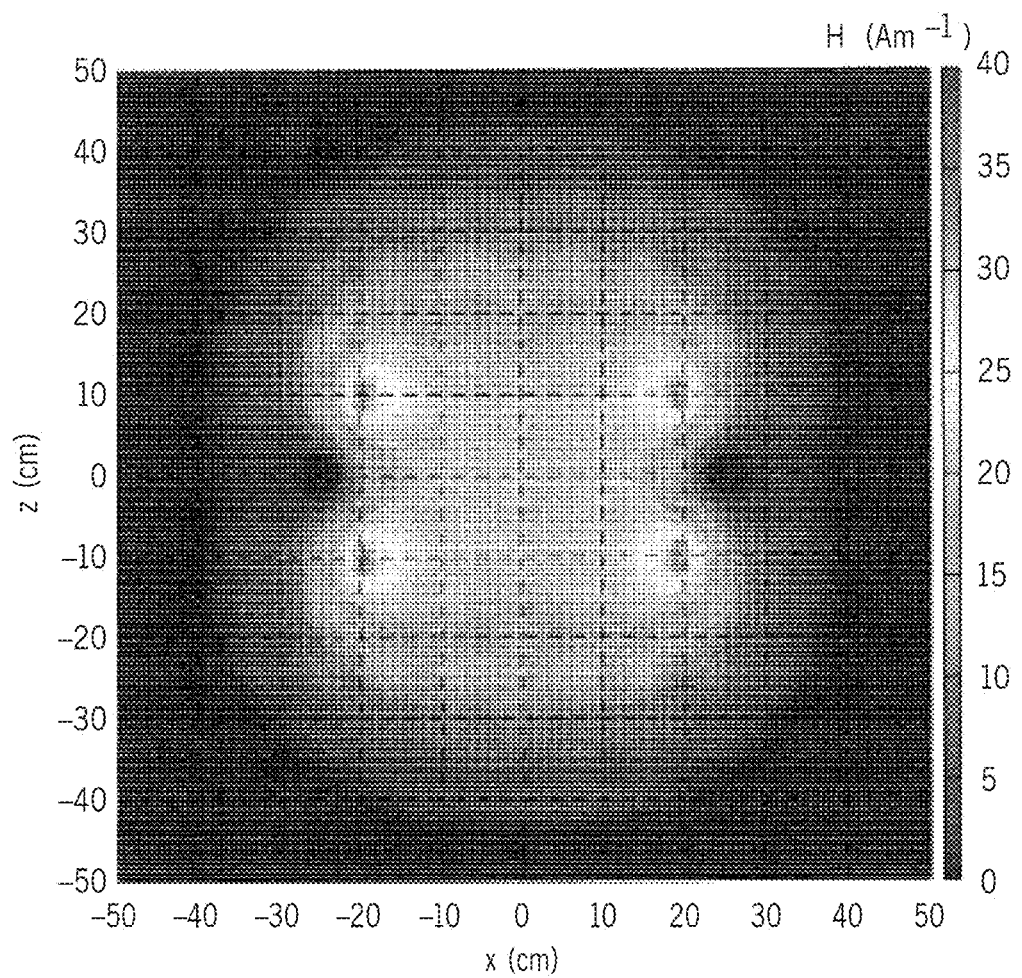
FIG. 15 shows an $H_z$ field calculated based on a three dimensional finite elements analysis simulation of a transmitter coil implemented in accordance with some embodiments of the disclosed subject matter.

FIG. 15 shows an $H_z$ field calculated based on a three dimensional finite elements analysis simulation of a transmitter coil implemented in accordance with some embodiments of the disclosed subject matter. A three-dimensional FEA simulation was performed using Maxwell simulation software to simulate a magnetic field produced by a Helmholtz transmitter coil described above in connection with FIG. 7C. FIG. 15 shows a cross section view of the $H_z$ field generated by the transmitter. As shown in FIG. 15, the magnetic field intensity is relatively uniform in the area surrounded by the coils.

Figure 16A:
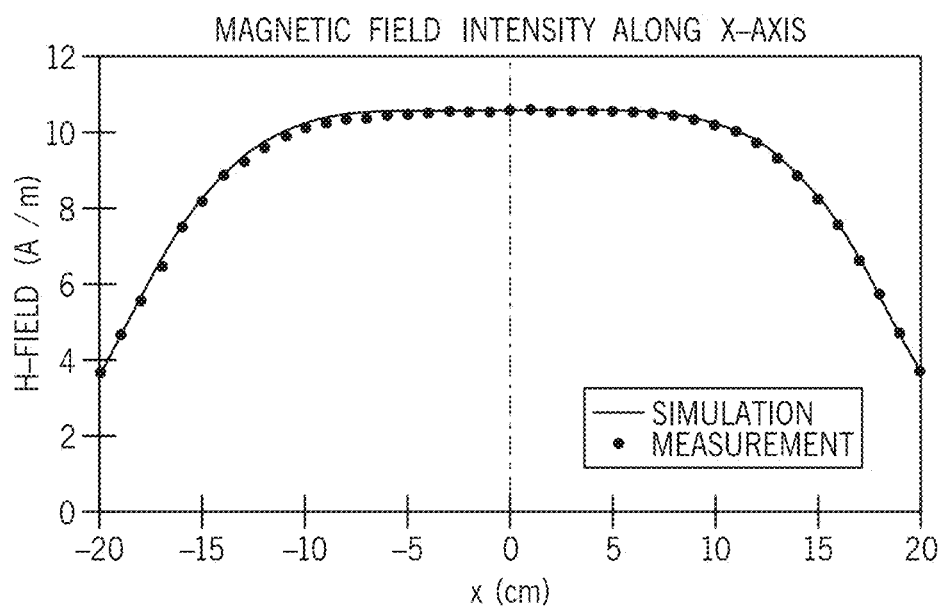
FIG. 16A shows a chart illustrating magnetic field intensity along the x-axis of a transmitter coil implemented in accordance with some embodiments of the disclosed subject matter.
Figure 16B:
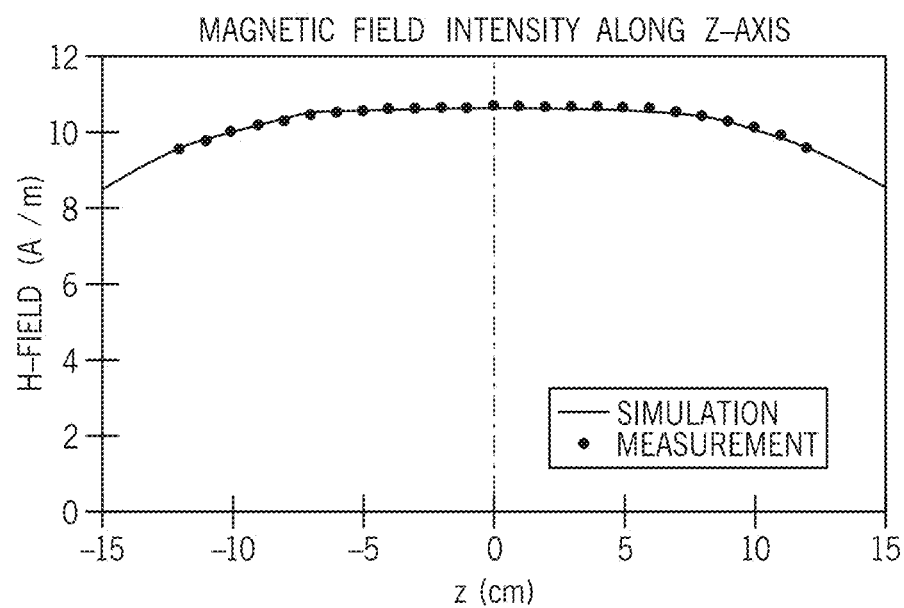
FIG. 16B shows a chart illustrating magnetic field intensity along the z-axis of a transmitter coil implemented in accordance with some embodiments of the disclosed subject matter.

FIGS. 16A and 16B show charts illustrating simulated and measured magnetic field intensity along the x-axis and z-axis, respectively, of a transmitter coil implemented in accordance with some embodiments of the disclosed subject matter. As shown in FIGS. 16A and 16B, the simulated and measured results are consistent with a tolerance of about 2.3%. All the plots reveal that the transmitter provides a relatively uniform $H_z$ field within a relatively large volume in the body. The charts of FIGS. 16A and 16B illustrate that the $H_z$ field deviation is less than about 4.5% within a range ±10 cm along the x-axis and about 6.2% along the z-axis.

Figure 17:
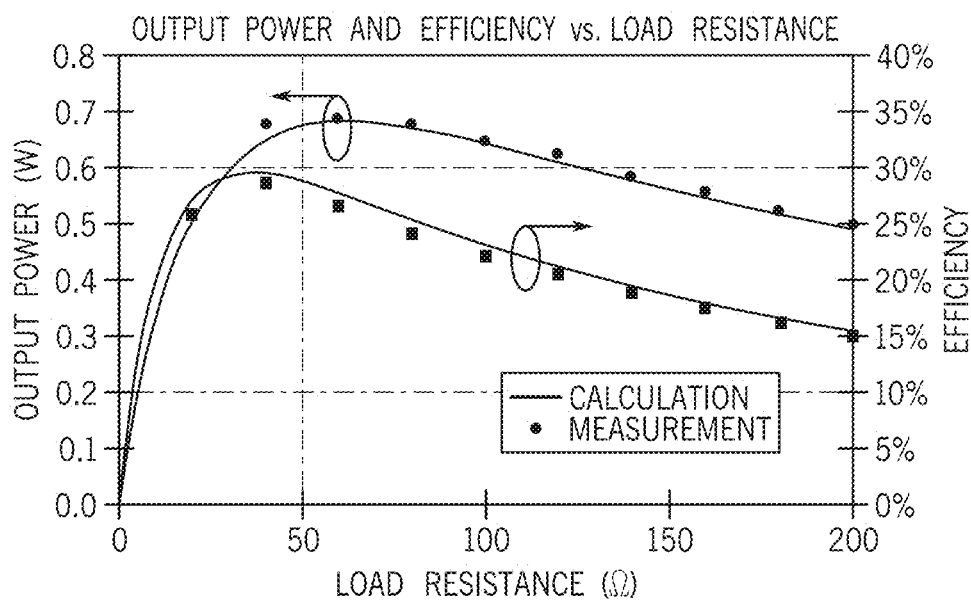
FIG. 17 shows a chart illustrating output power and efficiency of coupling between a transmitter coil and a receiving coil for a wireless radio frequency lesioning system implemented in accordance with some embodiments of the disclosed subject matter.

FIG. 17 shows a chart illustrating output power and efficiency of coupling between a transmitter coil and a receiving coil for a wireless radio frequency lesioning system implemented in accordance with some embodiments of the disclosed subject matter. As shown in FIG. 17, the output power and energy efficiency of the energy coupling system with different load resistance values were calculated and verified by measurement. In a test setup, a receiving coil was positioned in the middle of, and parallel to, the transmitter. The mutual inductance between the energy coupling coils was 8.85 nH. Since low-loss, high-frequency capacitors were used in the receiver's resonant network, the ESRs of the capacitors were negligible compared to the receiving coil resistance. The output power and efficiency were calculated using Equations (3) and (4), and measured with load resistance from 20Ω to 200Ω. The calculated and measured results are consistent with a tolerance of about 5.5% as shown in FIG. 17. Note that the desired load range for achieving optimal output power can be obtained by adjusting the capacitance values of $C_2$ and $C_3$ in the potential divider. In one particular implementation, the impedance of the RFL electrodes was between 55 and 80Ω when the electrodes were inserted into a piece of chicken muscle tissue, in which case capacitance values of $C_2$ and $C_3$ can be selected to achieve a maximum output power at $R_L$ 60Ω. From the calculated result in FIG. 17, although maximum output occurred at $R_L$=62Ω, high output power with 95% of the maximum value was achieved in a wide load range between 41Ω and 93Ω. At $R_L$=60Ω, the energy efficiency was about 27.8%, which was 1.7% lower than the maximum efficiency at $R_L$=36Ω.

Figure 18:
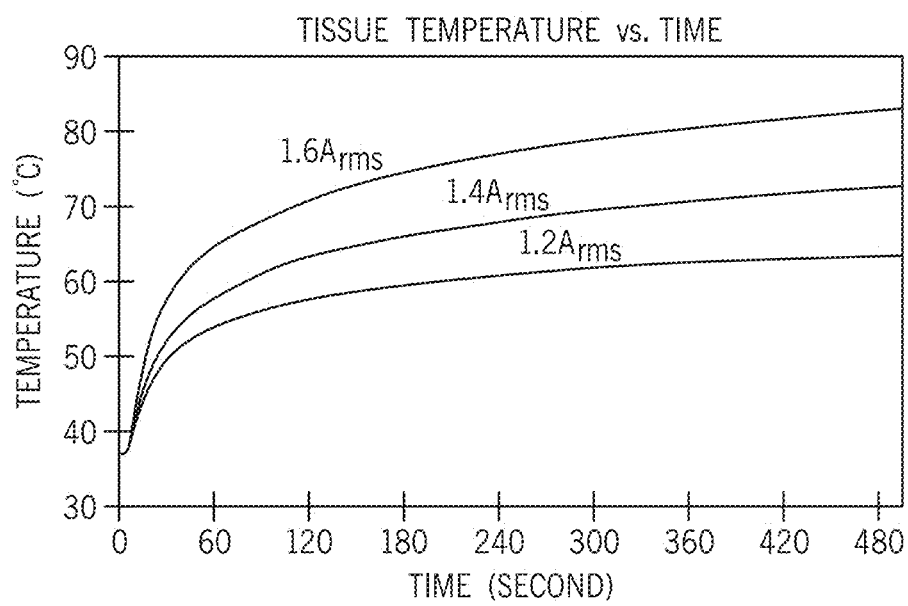
FIG. 18 shows a chart illustrating temperatures of muscle tissue over time for various excitation currents used to perform wireless radio frequency lesioning using a wireless radio frequency lesioning system implemented in accordance with some embodiments of the disclosed subject matter.

FIG. 18 shows a chart illustrating temperatures of muscle tissue over time for various excitation currents used to perform wireless radio frequency lesioning using a wireless radio frequency lesioning system implemented in accordance with some embodiments of the disclosed subject matter. An implantable RFL device wirelessly powered by a segmented coil transmitter was tested using ex-vivo chicken muscle tissue with the energy-receiving coil located at the middle of the transmitter, and with the exposed parts of the RFL electrodes entirely surrounded by chicken muscle tissue. A temperature therapy pad was operated under the chicken muscle tissue to preheat and maintain the muscle at 37° C., by circulating hot water with temperature control.

Throughout the experiment, the muscle temperature was recorded with a thermocouple sensor, with placement of the sensor based on the RFL simulation result described above in connection with FIGS. 14A-14C, which showed that the current density was mainly concentrated between the bipolar RFL electrodes and the maximum current density occurred around the electrodes. The thermocouple sensor was placed midway between the electrodes to ensure the temperature of the tissue in the whole target region was equal to or higher than the measured temperature. In conventional RFL operations, the electrode temperature is about 80° C. and the lesioned region boundary temperature is 55° C., at which biological tissue is considered lesioned. Different transmitter excitation current levels were applied to determine the required excitation current and time to achieve tissue lesioning. The electrode voltage $V_{out}$, current $I_{out}$, and power $P_{out}$ with excitation current $I_t$ of 1.2 $A_{rms}$, 1.4 $A_{rms}$, and 1.6 $A_{rms}$ were measured and are tabulated in Table 1 below. The electrode voltage and power ranged from about 8.28 $V_{rms}$ to about 11.24 $V_{rms}$, and 0.89 W to 1.62 W, respectively. In each experiment, the transmitting coil was excited for 500 seconds. The measured muscle temperatures versus time are shown in the chart in FIG. 18. The result shows that the tissue temperature increased with increasing excitation current and time. After 500 seconds of 1.6 $A_{rms}$ excitation, the tissue temperature increased to 83.3° C. which is more than sufficient for tissue lesioning. Even with a lower excitation of 1.2 $A_{rms}$ for 73 seconds, the tissue temperature increased to about 55° C., at which the tissue is considered lesioned. Although the lower excitation can achieve tissue lesioning, in actual RFL procedures blood flow would likely remove heat via forced convection, so the required excitation level and duration would likely be higher. When the transmitting coil current increased from 1.2 $A_{rms}$ to 1.6 $A_{rms}$, the lesioned tissue footprint increased from about 7 mm×3.4 mm to 12 mm×11 mm, and the depth increased from 2.5 mm to 4.8 mm.

TABLE 1

| | | | |
|---|---|---|---|
| Transmitter Current, $I_t$ ($A_{rms}$) | 1.2 | 1.4 | 1.6 |
| Electrode Voltage, $V_{out}$ ($V_{rms}$) | 8.28 | 10.0 | 11.24 |
| Electrode Current, $I_{out}$ ($I_{rms}$) | 0.108 | 0.125 | 0.144 |
| Electrode Power, $P_{out}$ (W) | 0.89 | 1.25 | 1.62 |

Figure 19A:
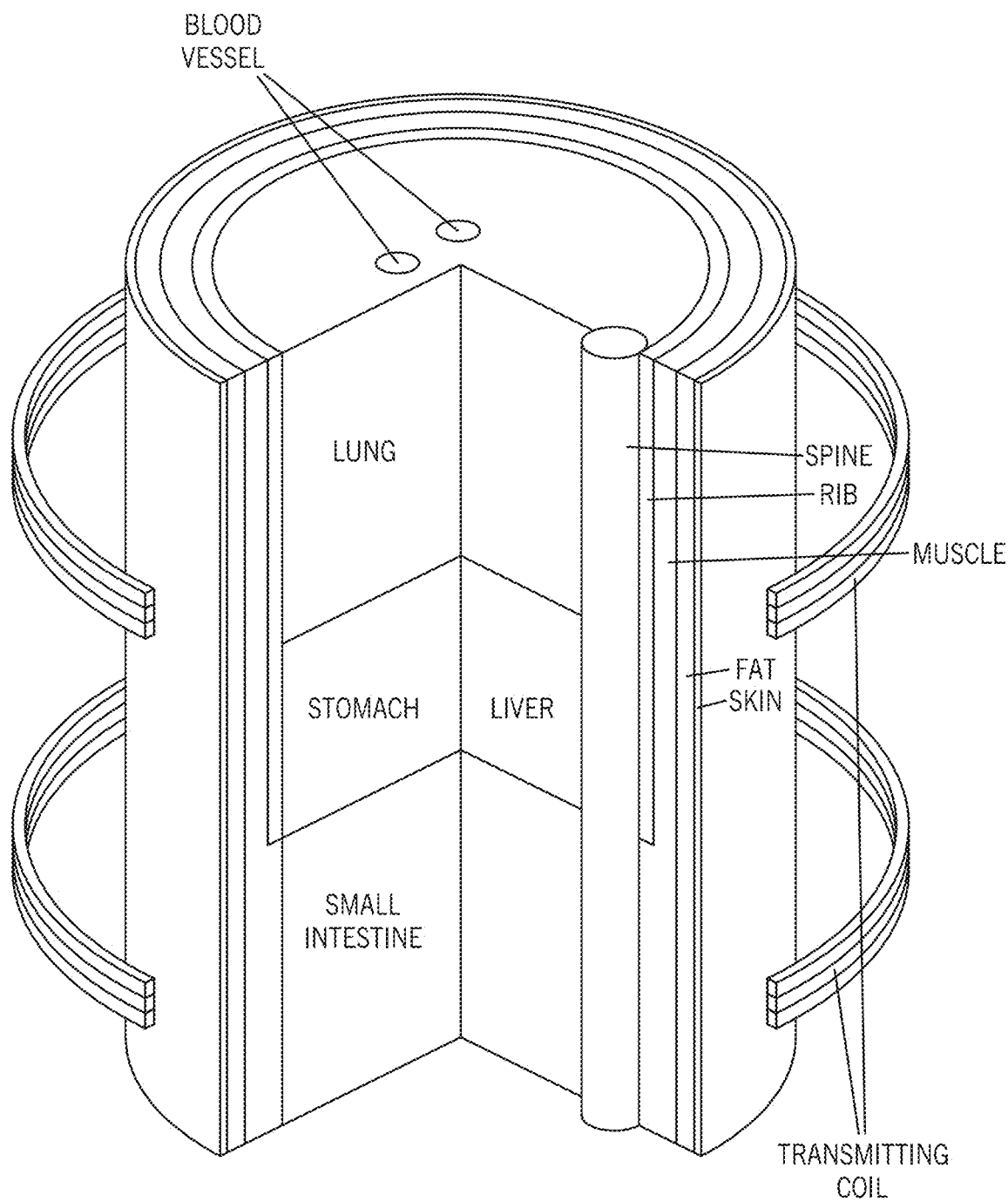
FIG. 19A shows a cross-sectional view of a finite element analysis model for evaluating specific energy absorption rate caused by exposure to a transmitter coil implemented in accordance with some embodiments of the disclosed subject matter.
Figure 19B:
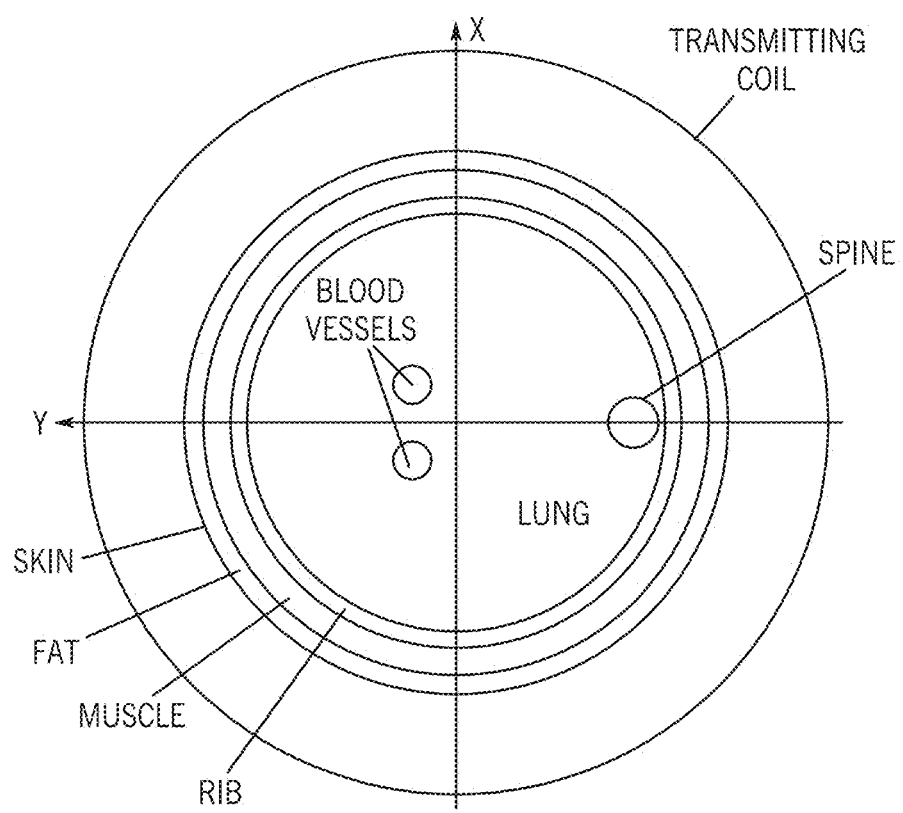
FIG. 19B shows a top-down view of the finite element analysis model for evaluating specific energy absorption rate caused by exposure to a transmitter coil implemented in accordance with some embodiments of the disclosed subject matter.

FIGS. 19A and 19B show a cross-sectional view and a top-down view of a finite element analysis model for evaluating specific energy absorption rate caused by exposure to a transmitter coil implemented in accordance with some embodiments of the disclosed subject matter. FIGS. 19A and 19B show a simulation model of a human torso used in an FEA simulation for evaluating the energy absorption in a human body caused by the magnetic field generated by the transmitting coil. The simulation model is similar to a model previously used in a wirelessly powered heart pump system, in which the magnetic field generated by the transmitting coil is concentrated around the patient's thorax, and the interior of the model was filled with material simulating the electrical properties of human lung. In the treatment of chronic low back pain, as an example, the 40-cm Helmholtz coil energy transmitter would wrap around the middle of the patient's torso, and organs in the abdomen (e.g., the stomach, liver, and intestines) would be exposed to the magnetic field. Accordingly, the FEA model was modified to include the abdomen as illustrated in FIG. 19A. Stomach, liver and small intestine are included to simulate a human abdomen because they occupy a large volume there, and the lower part of the torso model was filled with materials simulating these abdominal organs and the height of the lung portion was modified to 15 cm. The stomach and liver portions were modeled using half-cylindrical shape with heights of 10 cm. The small intestine portion was modeled using a cylindrical shape with a height 15 cm. The electrical properties of the tissues used in the FEA model at 6.78 MHz are listed below in Table 2. The tissue conductivity and relative permittivity were obtained on the basis of the 4-Cole-Cole Model using the RF_Tools MATLAB program developed by the Center for NMR Research at Penn State University. From the FEA simulation, the power absorption density in the torso model was obtained. The SAR was deduced from the power absorption density by the relationship $$SAR (W kg^{-1}) = \frac{Power\ absoprtion\ density\ (W m^{-3})}{Mass\ density\ (kg m^{-3})} \quad (7)$$

TABLE 2

| | Conductivity (S m$^{-1}$) | Relative permittivity | Mass Density (kg m$^{-3}$) |
|---|---|---|---|
| Blood | 1.0673 | 421.67 | 1060 |
| Bone | 0.11585 | 89.923 | 1330 |
| Fat | 0.027776 | 16.318 | 960 |
| Liver | 0.2936 | 296.9 | 1092 |
| Lung | 0.21036 | 175.97 | 246 |
| Muscle | 0.6021 | 233.27 | 1065 |
| Skin | 0.14692 | 478.4 | 1090 |
| Small Intestine | 1.2883 | 737.44 | 1044 |
| Stomach | 0.75747 | 359.26 | 1065 |

Figure 20:
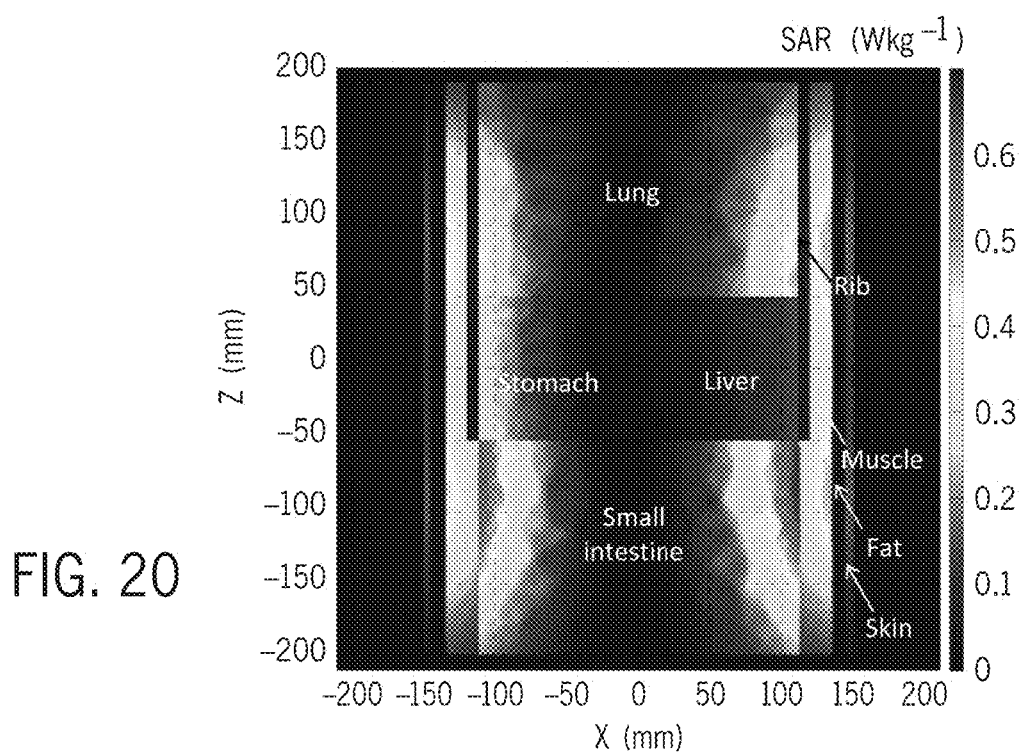
FIG. 20 shows a chart illustrating simulated specific energy absorption rate on the x-z plate at y=0 caused by exposure to a transmitter coil implemented in accordance with some embodiments of the disclosed subject matter.

FIG. 20 shows a chart illustrating simulated specific energy absorption rate on the x-z plate at y=0 caused by exposure to a transmitter coil implemented in accordance with some embodiments of the disclosed subject matter. The chart of FIG. 20 shows the simulated SAR when the transmitting coil current was 1 $A_{rms}$. As shown above in Table 2, small intestine has the highest conductivity among the tissues in the FEA model, so maximum SAR (0.69 W $kg^{-1}$) occurs in the small intestine close to the transmitting coil. Based on guidelines from the International Commission on Non-Ionizing Radiation Protection (ICNIRP), the localized SAR should be lower than 2 W $kg^{-1}$ to avoid undesired tissue damage. Since SAR is proportional to the square of the excitation current, the maximum allowable transmitting current would be about 1.70 $A_{rms}$ based on these results. Note that, from the result of ex-vivo chicken muscle tissue lesioning experiments, the excitation current required to lesion muscle is lower than 1.70 $A_{rms}$. As a result, the SAR caused by the energy transmitter is expected to be lower than the suggested maximum of 2 W $kg^{-1}$.

Note that, although the mechanisms described herein are described in connection with nerve tissue lesioning, the mechanisms can be used in other applications, such as serial tumor ablation in which a wireless RFL device is implanted within or near a tumor, and is used periodically (e.g., at regular or irregular intervals) to damage the tissue of the tumor.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any other suitable media that is fleeting and devoid of any semblance of permanence during transmission, and/or any suitable intangible media.

It will be appreciated by those skilled in the art that while the disclosed subject matter has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is hereby incorporated by reference, as if each such patent or publication were individually incorporated by reference herein.

Various features and advantages of the invention are set forth in the following claims.

The invention claimed is:

1. A wireless radiofrequency device, comprising:
   a receiving coil;
   a plurality of capacitors coupled in parallel to the receiving coil;
   a first electrode; and
   a second electrode, wherein a capacitor of the plurality of capacitors is connected between the first electrode and the second electrode, and wherein capacitances of the plurality of capacitors cause the receiving coil to pair with a transmitter at an operating frequency, wherein the wireless radiofrequency device is configured to generate an induced current in the receiving coil responsive to receiving a first signal at the operating frequency thereby causing an induced second signal that is transmitted between the first electrode and the second electrode via tissue proximate the first electrode and the second electrode with power sufficient to cause an increase in temperature of the tissue.

2. The wireless radiofrequency device of claim 1, wherein the plurality of capacitors comprises:
   a first capacitor connected in parallel with the receiving coil;
   a second capacitor and the capacitor connected in series with one another, the second capacitor and the capacitor connected in parallel with the first capacitor and with the receiving coil.

3. The wireless radiofrequency device of claim 2, wherein the second capacitor and the capacitor form a potential divider to provide a first portion of an input potential to the first electrode and a second portion of the input potential to the second electrode.

4. The wireless radiofrequency device of claim 1, wherein the receiving coil comprises a plurality of turns.

5. The wireless radiofrequency device of claim 4, wherein each turn comprises a plurality of enameled wires connected in parallel.

6. The wireless radiofrequency device of claim 1, wherein the operating frequency is about 6.78 megahertz (MHz).

7. The wireless radiofrequency device of claim 1, wherein the plurality of capacitors comprise capacitors with capacitances of 6 nanofarads, 470 picofarads, and 638 picofarads.

8. The wireless radiofrequency device of claim 1, wherein the first electrode comprises a wire connected to between two of the plurality of capacitors at a first end, and terminating at a second end without connecting to another component.

9. The wireless radiofrequency device of claim 8, wherein the first electrode comprises a wire having a diameter of between about 30 American wire gauge (AWG) and about 10 AWG.

10. The wireless radiofrequency device of claim 8, wherein a first portion of the first electrode extending from the first end is insulated, and a second portion extending from the second end toward the first portion is not insulated.

11. The wireless radiofrequency device of claim 1, wherein the receiving coil has an exterior diameter of less than 2.5 centimeters.

12. The wireless radiofrequency device of claim 1, wherein the first electrode and the second electrode are separated by a gap.

13. The wireless radiofrequency device of claim 12, wherein the gap is about 5 millimeters.

14. The wireless radiofrequency device of claim 1, wherein the wireless radiofrequency device is configured to be implanted in a subject adjacent to tissue to be lesioned, and to wirelessly receive power from a radio transmitter which causes tissue between and around the electrodes to be heated to at least 55 degrees Celsius.

15. The wireless radiofrequency device of claim 1, further comprising:
   a temperature sensor that outputs a temperature signal; and
   a switch that, when closed, causes an electrical component to be connected in parallel with the receiving coil, wherein a state of the switch is controlled based on the temperature signal.

16. The wireless radiofrequency device of claim 15, wherein the electrical component has an impedance that, when connected in parallel with the receiving coil, causes the receiving coil to be detuned from the operating frequency.

17. The wireless radiofrequency device of claim 1, wherein the first electrode is disposed at a first end of the receiving coil.

18. The wireless radiofrequency device of claim 1,
wherein the wireless radiofrequency device is a passive device that is powered wirelessly entirely by an external power source, and
wherein a power of the induced second signal is at least 0.89 watts (W).

19. A wireless radiofrequency device, comprising:
a first loop comprising:
 a receiving coil having a first end and a second end; and
 a first capacitor connected between the first end of the receiving coil and the second end of the receiving coil; and
a second loop comprising:
 the receiving coil;
 a second capacitor connected between the first end of the receiving coil and a first end of a first electrode; and
 a third capacitor connected between the first electrode and the second end of the receiving coil, and connected between the second capacitor and the second end of the receiving coil; and
a second electrode having a first end connected to the second end of the receiving coil and the third capacitor, wherein a connection is formed between the first electrode and the second electrode through tissue of a subject in which the wireless radiofrequency device is implanted.

20. A wireless radiofrequency system, comprising:
a wireless radiofrequency device, comprising:
 a receiving coil;
 a plurality of capacitors coupled in parallel to the receiving coil;
 a first electrode; and
 a second electrode, wherein a capacitor of the plurality of capacitors is connected between the first electrode and the second electrode, and wherein capacitances of the plurality of capacitors cause the receiving coil to pair with a transmitter at an operating frequency;
a transmitter comprising at least one transmitting coil;
a radiofrequency generator configured to apply a radiofrequency signal at the operating frequency to the transmitter; and
a processor operatively coupled to the transmitter and the radiofrequency generator, wherein the processor is configured to:
 cause the radiofrequency generator to apply a first radiofrequency signal at the operating frequency to the at least one transmitting coil to produce a magnetic field at the operating frequency in a vicinity of the at least one transmitting coil,
  wherein the magnetic field is configured to induce a current in the receiving coil of the wireless radiofrequency device, thereby causing an induced second radiofrequency signal that is transmitted between the first electrode and the second electrode via tissue proximate the first electrode and the second electrode with power sufficient to cause an increase in temperature of the tissue.

21. The wireless radiofrequency system of claim 20, wherein the at least one transmitting coil comprises at least one turn that is segmented by at least one capacitor connected between adjacent segments.

22. The wireless radiofrequency system of claim 21, wherein the at least one turn is segmented into four segments, and comprises four 765 picofarad resonant capacitors each connecting two adjacent segments.

23. The wireless radiofrequency system of claim 20, wherein the at least one transmitting coil comprises a first transmitting coil and a second transmitting coil arranged to form a Helmholtz coil.

24. The wireless radiofrequency system of claim 20, wherein the radiofrequency signal has a root mean square current of less than about 1.7 amperes ($A_{rms}$).

25. The wireless radiofrequency system of claim 20,
wherein the wireless radiofrequency device is a passive device that is powered wirelessly entirely by an external power source,
wherein the first radiofrequency signal has a root mean square current of at least 1.2 amperes ($A_{rms}$); and
wherein a power of the induced second radiofrequency signal is at least 0.89 watts (W).

* * * * *

UNITED STATES PATENT AND TRADEMARK OFFICE
CERTIFICATE OF CORRECTION

PATENT NO. : 11,006,998 B2
APPLICATION NO. : 15/885739
DATED : May 18, 2021
INVENTOR(S) : Sai Chun Tang et al.

It is certified that error appears in the above-identified patent and that said Letters Patent is hereby corrected as shown below:

In the Specification

Column 13, Lines 57-64, should be deleted.

Column 19, Line 6, "$R_L$ 60Ω" should be -- $R_L \approx 60Ω$ --.

Column 20, Line 4, "$I_{out}(I_{rms})$" should be -- $I_{out}(A_{rms})$ --.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*